US010668224B2

(12) United States Patent
Gylleby et al.

(10) Patent No.: US 10,668,224 B2
(45) Date of Patent: Jun. 2, 2020

(54) MEDICAMENT DELIVERY DEVICE

(71) Applicant: CAREBAY EUROPE LTD, Sliema (MT)

(72) Inventors: Stefan Gylleby, Stockholm (SE); Rasmus Renstad, Stockholm (SE); Daniel Säll, Segeltorp (SE)

(73) Assignee: SHL MEDICAL AG, Zug (CH)

( * ) Notice: Subject to any disclaimer, the term of this patent is extended or adjusted under 35 U.S.C. 154(b) by 216 days.

(21) Appl. No.: 15/755,741

(22) PCT Filed: Aug. 30, 2016

(86) PCT No.: PCT/EP2016/070373
§ 371 (c)(1),
(2) Date: Feb. 27, 2018

(87) PCT Pub. No.: WO2017/045908
PCT Pub. Date: Mar. 23, 2017

(65) Prior Publication Data
US 2018/0243511 A1     Aug. 30, 2018

(30) Foreign Application Priority Data
Sep. 14, 2015  (EP) .................................... 15184984

(51) Int. Cl.
*A61M 5/31*   (2006.01)
*A61M 5/20*   (2006.01)
(Continued)

(52) U.S. Cl.
CPC ........ *A61M 5/3157* (2013.01); *A61M 5/2033* (2013.01); *A61M 5/3158* (2013.01);
(Continued)

(58) Field of Classification Search
CPC .............. A61M 5/3157; A61M 5/2033; A61M 5/31515; A61M 5/31568; A61M 5/3158; A61M 5/31583
See application file for complete search history.

(56) References Cited

U.S. PATENT DOCUMENTS

| | | | |
|---|---|---|---|
| 8,361,026 B2 | 1/2013 | Edwards et al. | |
| 2002/0188419 A1* | 12/2002 | Slate .................. | A61M 5/20 702/176 |

(Continued)

FOREIGN PATENT DOCUMENTS

| | | |
|---|---|---|
| CN | 102099069 B | 11/2013 |
| JP | 2012-507314 A | 3/2012 |

(Continued)

OTHER PUBLICATIONS

International Search Report and Written Opinion for Int. App. No. PCT/EP2016/070373, dated Dec. 9, 2016.

*Primary Examiner* — Manuel A Mendez
*Assistant Examiner* — Courtney B Fredrickson
(74) *Attorney, Agent, or Firm* — McDonnell Boehnen Hulbert & Berghoff LLP

(57) ABSTRACT

A medicament delivery device is presented having a housing arranged to accommodate a medicament container, a drive mechanism capable of, upon activation, act on the medicament container, a communication unit arranged in the housing, a switch operably connectable to the drive mechanism and connected to the communication unit for activating the communication unit when operated, wherein the switch is operated by the drive mechanism at the end of a dose delivery sequence.

19 Claims, 24 Drawing Sheets

(51) Int. Cl.
  *A61M 5/315* (2006.01)
  *A61M 5/24* (2006.01)
  *A61M 5/32* (2006.01)

(52) U.S. Cl.
  CPC .... *A61M 5/31515* (2013.01); *A61M 5/31568* (2013.01); *A61M 5/31593* (2013.01); *A61M 5/20* (2013.01); *A61M 5/24* (2013.01); *A61M 5/326* (2013.01); *A61M 2205/14* (2013.01); *A61M 2205/33* (2013.01); *A61M 2205/3561* (2013.01); *A61M 2205/3569* (2013.01); *A61M 2205/3584* (2013.01); *A61M 2205/50* (2013.01); *A61M 2205/52* (2013.01); *A61M 2205/581* (2013.01); *A61M 2205/582* (2013.01); *A61M 2205/583* (2013.01)

(56) References Cited

U.S. PATENT DOCUMENTS

2009/0030366 A1* 1/2009 Hochman ............... A61M 5/20
                                                                                                    604/67
2014/0200510 A1   7/2014 Agard et al.
2014/0276583 A1* 9/2014 Chen .................. A61M 5/31546
                                                                                                    604/506

FOREIGN PATENT DOCUMENTS

| | | |
|---|---|---|
| JP | 2012-519028 A | 8/2012 |
| JP | 2014-517734 A | 7/2014 |
| TW | 201417853 A | 5/2014 |
| TW | 201431577 A | 8/2014 |
| TW | 201503923 A | 2/2015 |
| TW | 201509458 A | 3/2015 |
| TW | 201509467 A | 3/2015 |
| TW | 201521808 A | 6/2015 |
| WO | 2006/021932 A1 | 3/2006 |
| WO | 2009/083600 A1 | 7/2009 |
| WO | 2010/052275 A2 | 5/2010 |
| WO | 2010/098931 A1 | 9/2010 |
| WO | 2012/140097 A2 | 10/2012 |
| WO | 2015/011787 A1 | 1/2015 |

* cited by examiner

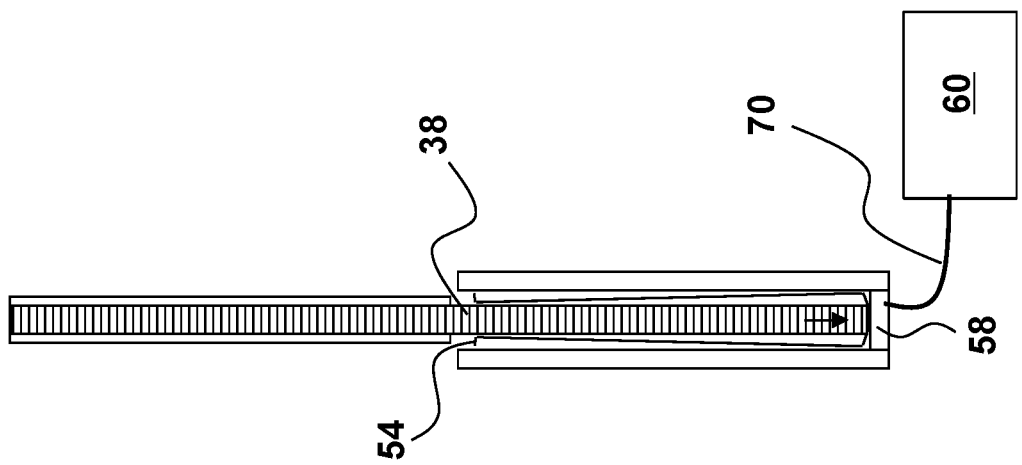
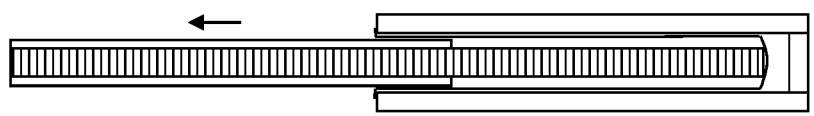
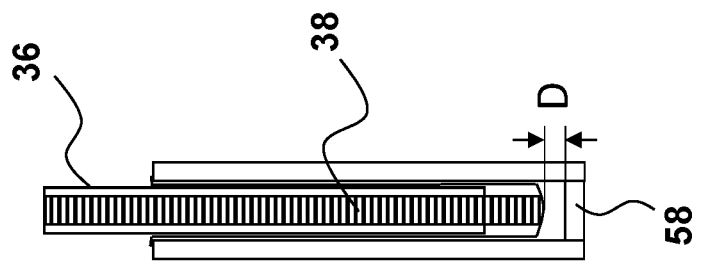

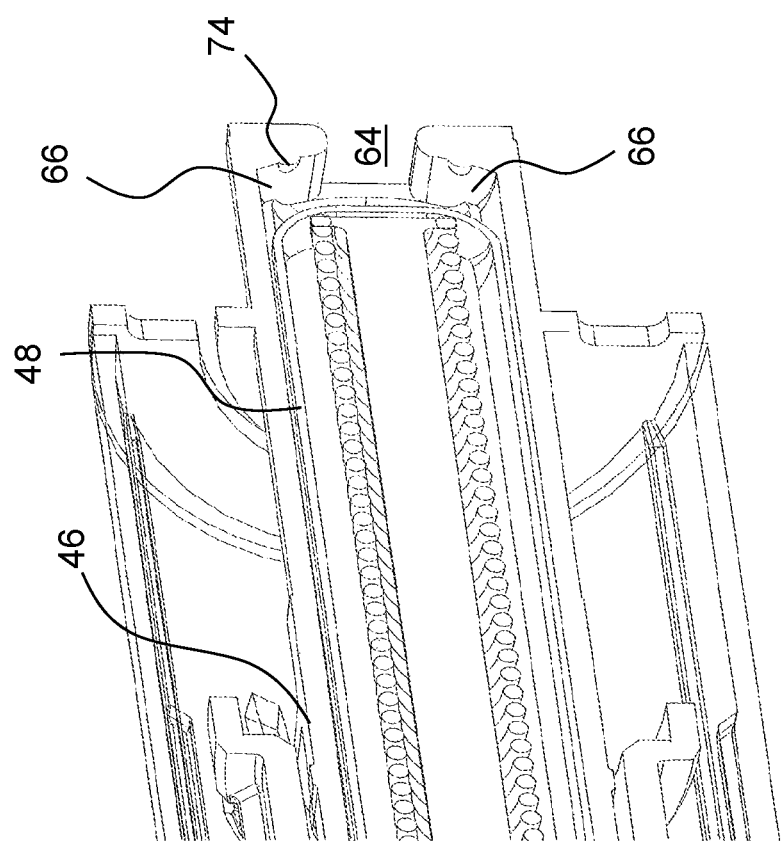
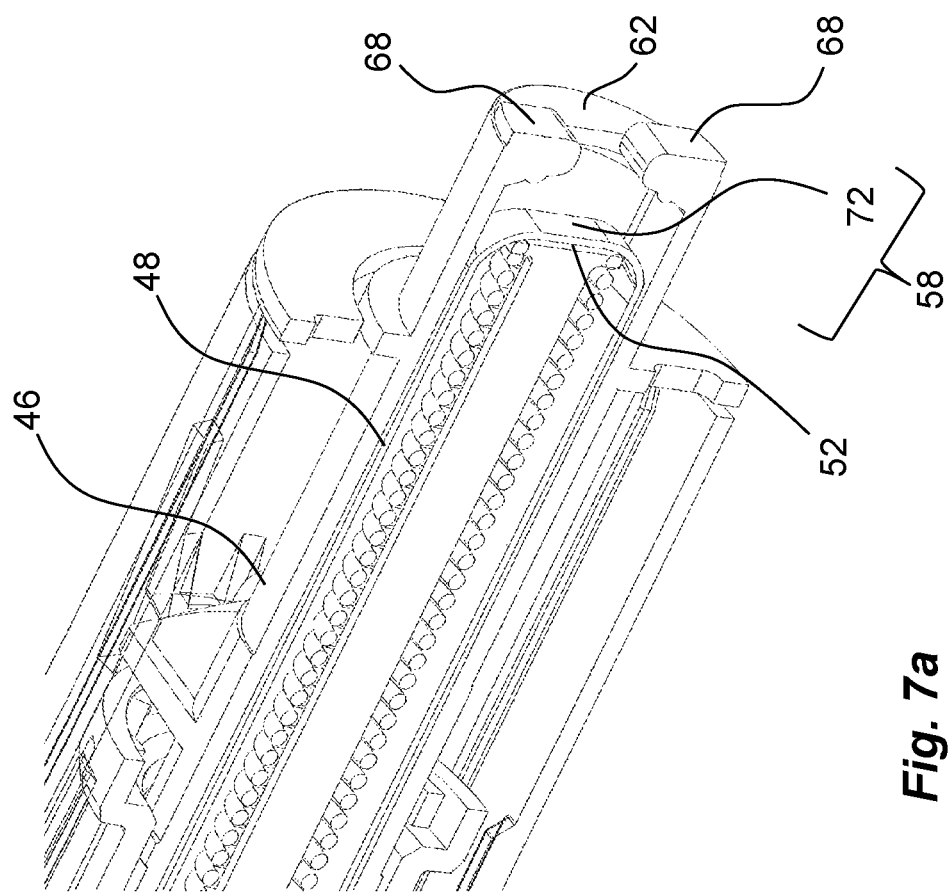
*Fig. 7b*
*Fig. 7a*

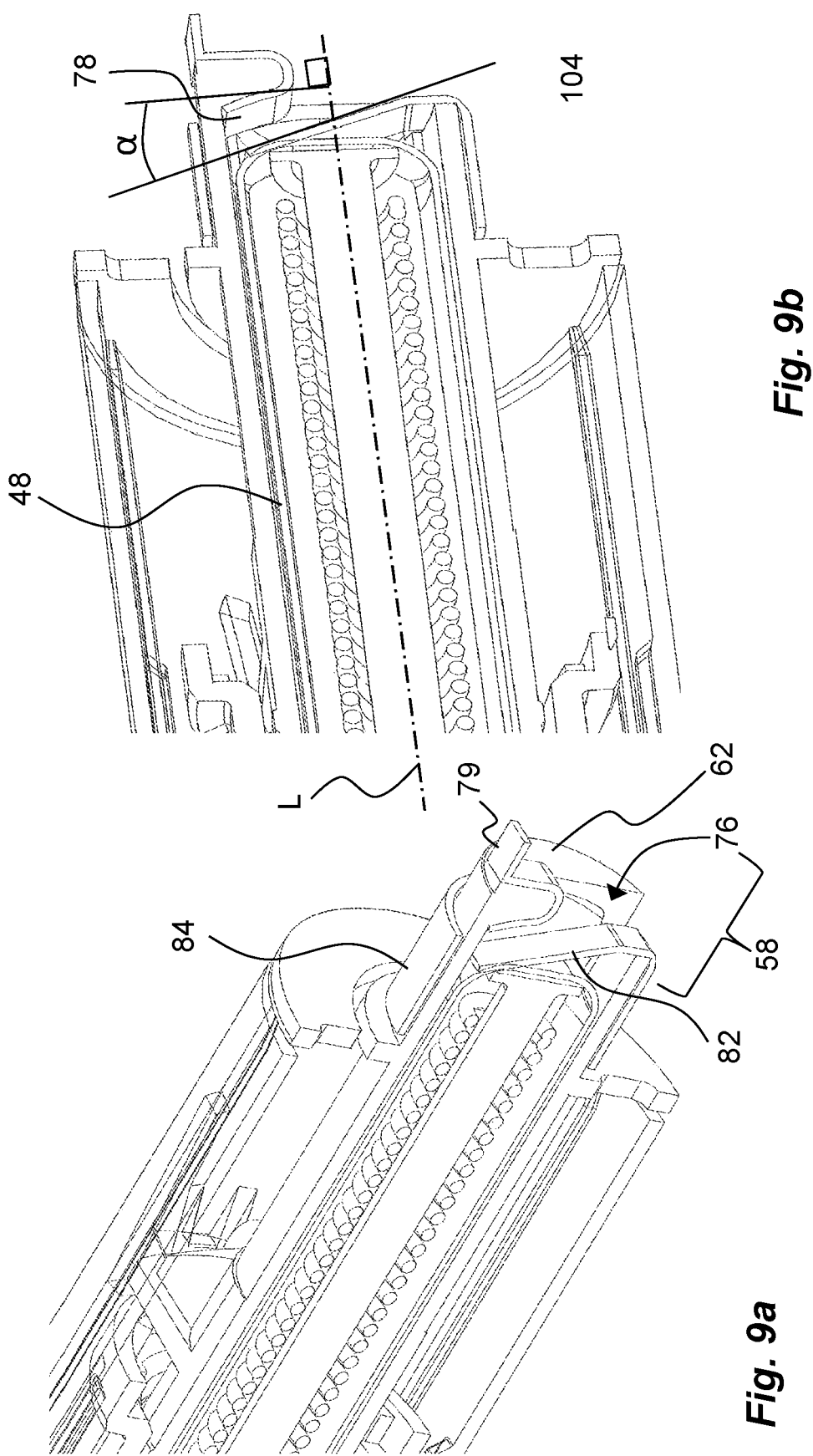

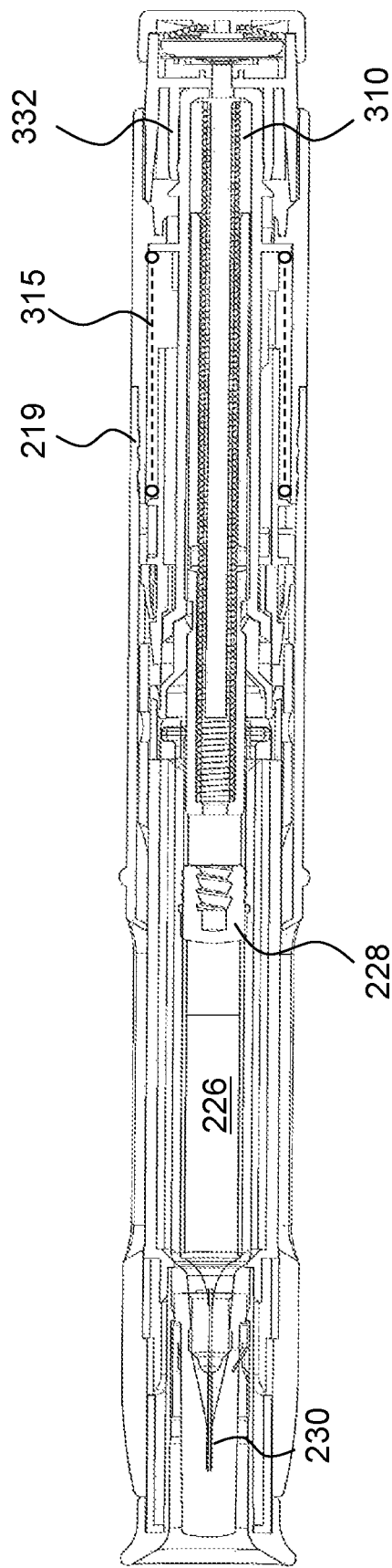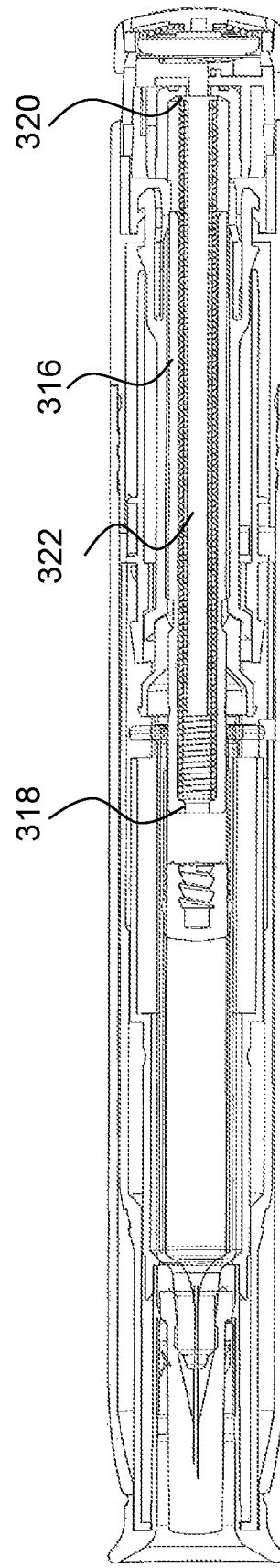
Fig. 17a
Fig. 17b

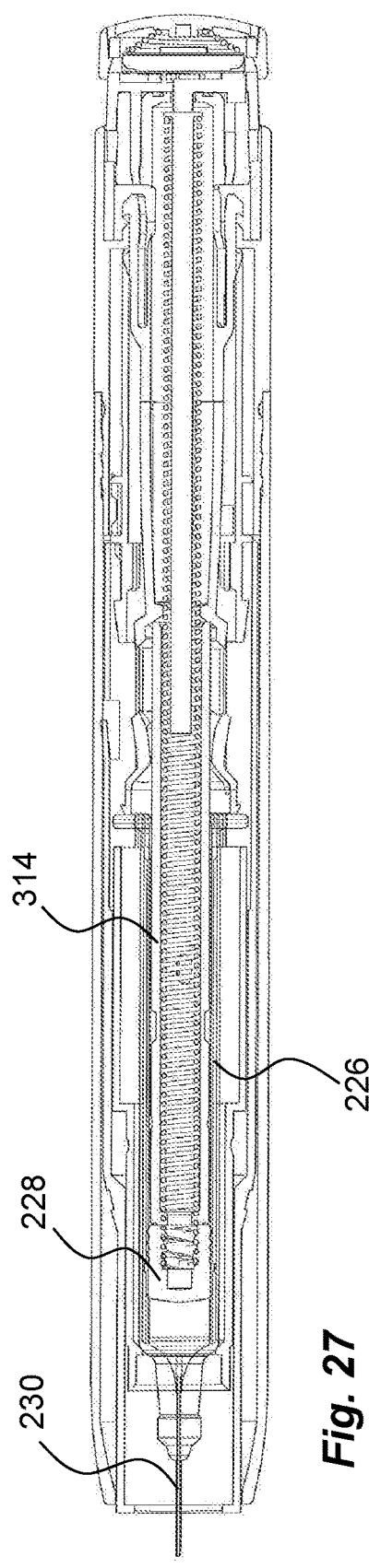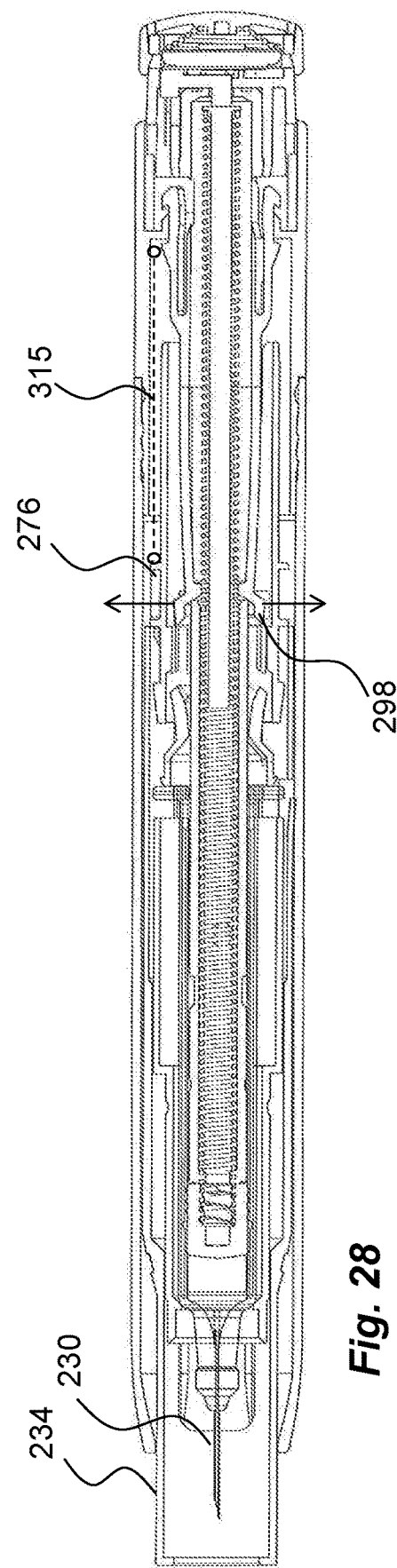
Fig. 27
Fig. 28

MEDICAMENT DELIVERY DEVICE

CROSS REFERENCE TO RELATED APPLICATIONS

The present application is a U.S. National Phase Application pursuant to 35 U.S.C. § 371 of International Application No. PCT/EP2016/070373 filed Aug. 30, 2016, which claims priority to European Patent Application No. 15184984.1 filed Sep. 14, 2015. The entire disclosure contents of these applications are herewith incorporated by reference into the present application.

TECHNICAL FIELD

The present disclosure relates to a medicament delivery device that is provided with communication capabilities.

BACKGROUND

There is a constant development of medicament delivery devices that are intended and designed to be used and handled by users that are not qualified nursing staff or physicians, i.e. handled by the patients themselves. Because the patients themselves handle the treatment, based on a specific treatment scheme, the physicians treating the patient have no direct information that the treatment schemes are followed as prescribed.

In order to obtain more information regarding the treatment, a number of devices have been developed that are capable of monitoring the dose delivery operations and to store this information. Some devices are also capable of transmitting the information to external storage locations that are accessible to a trained healthcare staff. This enables access to relevant dose delivery information to e.g. a physician of a patient.

Document U.S. Pat. No. 8,361,026 discloses a medicament delivery device that is arranged with a number of intelligent functions that may monitor the operation of the device. Among the functions are monitoring of appliance and/or adherence of the patient and uploading of the information to a suitable storage means of a remote device, where the latter could be a remote communication network, a computer, a smart phone, personal digital assistant, etc. Information could also be downloaded to the medicament delivery device to be accessible to the user, such as if the drug of a medicament in the device has been recalled by the manufacturer of the drug, that the drug has expired or updated user information. In this regard, the device is arranged with a number of switches that are activated during different functional stages.

In order for the device to function it is energized before use by pressing a start button, thus requiring a specific handling step in order to be able to use the device. Further, when the device is energized, its different electronics components and many functions will consume energy. This may be a pronounced drawback if the device is energized but not used directly for some reason. There is further a risk that the start button is operated unintentionally, thereby energizing the device by accident. If the device then is to be used at a later state, the power source of the device may be depleted of power.

SUMMARY

The aim of the present disclosure is to remedy the drawbacks of the state of the art medicament delivery devices. This aim is obtained by a medicament delivery device comprising the features of the independent patent claim. Preferable embodiments of the disclosure form the subject of the dependent patent claims.

According to one aspect of the disclosure the medicament delivery device may comprise a housing, which housing is arranged to accommodate a medicament container. Further a drive mechanism is arranged, comprising a drive force element capable of, upon activation, acting on the medicament container for expelling a dose of medicament from the medicament container.

Further, the medicament delivery device may comprise a communication unit associated with the housing, which communication unit is arranged to communicate different information to external information receivers and information storage sources. In this respect, the communication unit may comprise a switch operably connectable to the drive mechanism and connected to the communication unit for activating the communication unit when operated, wherein the switch is operated by the drive mechanism during a dose delivery sequence. This solution enables information to be transmitted from the communication unit when a dose delivery operation is performed. This information may be used in numerous ways for monitoring the use of the medicament delivery device. In this respect, monitoring of a dose delivery sequence is one of the better occurrences when a medicament delivery device is used. It is of course possible to monitor other functions such as removal of a safety cap and the like, but there is a problem that a cap may be removed at one moment, but then not used for quite a long time, whereby there is a discrepancy between the monitoring time and date and the time and date of usage, if the medicament delivery device is used at all.

According to a favourable solution, the communications unit may be arranged movable in the longitudinal direction between a non-activated position and an activated position. The design is further such that the drive force element may be arranged to exert a force on the communications unit to be biased in the distal direction to a non-activated position. Also, an activation force element may be arranged to exert a force on the communications unit in the proximal direction, wherein the force exerted by the activation force is chosen such that the force exceeds the force from the drive force element during a dose delivery sequence, thereby moving the communication unit to an activated position.

Thus the force from the drive force element is balanced against the force of the activation force element. The force balancing feature has the advantage that it is possible to have a tolerance span between the available forces from both the drive force element and the activation force element without the risk of not activating the communication unit. This in turn enables the point where the force levels alter the balance such that the communication unit is activated to be chosen along the full movement or stroke of the drive mechanism when expelling a dose of medicament.

For instance the force exerted by the activation force may be chosen such that the force exceeds the force from the drive force element near the end of a dose delivery sequence, thereby moving the communication unit to an activated position. In order to ascertain that a user does not withdraw the medicament delivery device before the dose delivery sequence is completed, the communication unit may be arranged with some sort of delay in the sending of data or information to the appropriate receiver.

According to one solution, the switch may be positioned on a proximally directed surface of the monitoring unit. Further, the medicament delivery device may be arranged with a distally directed contact surface, wherein the switch is moved in contact with the contact surface when the monitoring unit is moved in the activated position. This provides a robust and simple solution to the activation of the communication unit.

The drive force element may in a feasible solution be a compression spring, and the medicament delivery device may further comprise a pushing element operably connected between a distal end of the compression spring and a proximally directed surface of the communication unit. If a compression spring is used the medicament delivery device may comprise a spring guide rod, which spring guide rod may be arranged with a support element at its distal end, wherein the compression spring rests against a proximally directed surface of the support element and wherein the pushing element is in contact with a distally directed surface of the support element. Thus the spring guide rod acts as a guide, as an end support for the drive spring and as a contact element for the pushing element.

In order to reduce the actions of the forces acting on the communication unit, the pushing element may be arranged with a number of generally radially extending arms, which arms are provided with distally extending protrusions for providing force distribution on the communication unit.

According to one aspect of the communication unit, it may be arranged to communicate directly with a user and in this aspect the communication may be performed audibly and/or visually. Further, the communication unit may be arranged to communicate via a smart device. According to yet an aspect, the communication unit may be arranged to communicate with wireless networks and/or mobile communication networks, comprising transmitting and receiving data.

The data that the communication unit can obtain and transmit can be used in a number of ways, for example the monitoring of patient adherence.

These and other aspects of, and advantages with, the present disclosure will become apparent from the following detailed description of the disclosure and from the accompanying drawings.

BRIEF DESCRIPTION OF DRAWINGS

In the following detailed description of the disclosure, reference will be made to the accompanying drawings, of which FIG. 6 shows schematically the activation of the communication unit, FIG. 7 shows a first embodiment of a switch comprised in the first embodiment of a medicament delivery device, FIG. 9 shows a second embodiment of a switch comprised in the first embodiment of a medicament delivery device, FIG. 17 shows cross-sectional views of the medicament delivery device of FIG. 16.

DETAILED DESCRIPTION

In the present application, the term "distal part/end" refers to the part/end of the device, or the parts/ends of the members thereof, which under use of the device, is located the furthest away from a delivery site of a patient. Correspondingly, the term "proximal part/end" refers to the part/end of the device, or the parts/ends of the members thereof, which under use of the device is located closest to the delivery site of the patient.

In the following description, the wording smart devices will be used. In this context, smart devices may include electronic devices that are provided with processors that are capable of running computer programs as well as storage space to store programs as well as data retrieved from different external sources. It is further to be understood that the smart devices are provided with communication systems that are capable of communicating with data networks in order to access different databases. It is to be understood that databases may be accessed via the interne, so called cloud services, and/or databases that are connected directly to and accessed via local area networks. It is further to be understood that the smart devices in this context comprise some sort of human-machine interface for two-way communication. The human-machine interface may comprise displays, keyboards, microphones, loudspeakers, I/O-ports for connection of peripherals. Further the smart devices may be provided with antennas for wireless communication with the networks. Also, the smart devices may be arranged with receiving and transmitting mechanisms capable of communicating with NFC tags as well as programs capable of establishing and handling the communication with the NFC tags.

Further, in the following description, the wording medicament delivery device will be used. In this context, medicament delivery devices may include a number of devices capable of delivering certain doses of medicament to a user, such as e.g. injection devices with or without injection needles, inhalers of all kinds, such as powder, aerosol driven, gas, nebulizers having mouth or nasal pieces, dispensers for medicament in tablet form, eye dispensers, etc. The medicament delivery devices may be of either disposable type or re-usable type and may be provided with medicament containers suitably arranged for specific drugs in specific forms.

Figure 1:
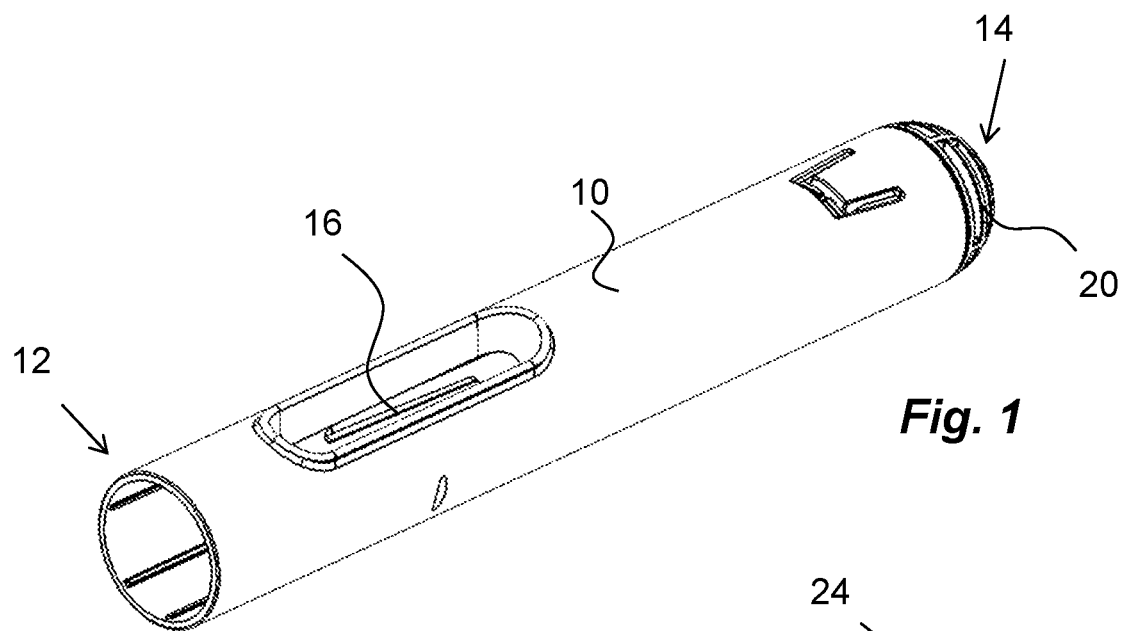
FIGS. 1 to 5 show detailed views of a first embodiment of a medicament delivery device comprising a communication unit.

As seen in FIG. 1, a medicament delivery device comprising the present disclosure may comprise a tubular housing 10 having a proximal end 12 and an opposite distal end 14. The housing 10 may further comprise a container holder 16 which is coaxially arranged within the housing for holding a medicament container 18, FIG. 3. The medicament delivery device further comprises an end cap 20 fixedly attached to the distal end 14 of the housing.

Figure 2:
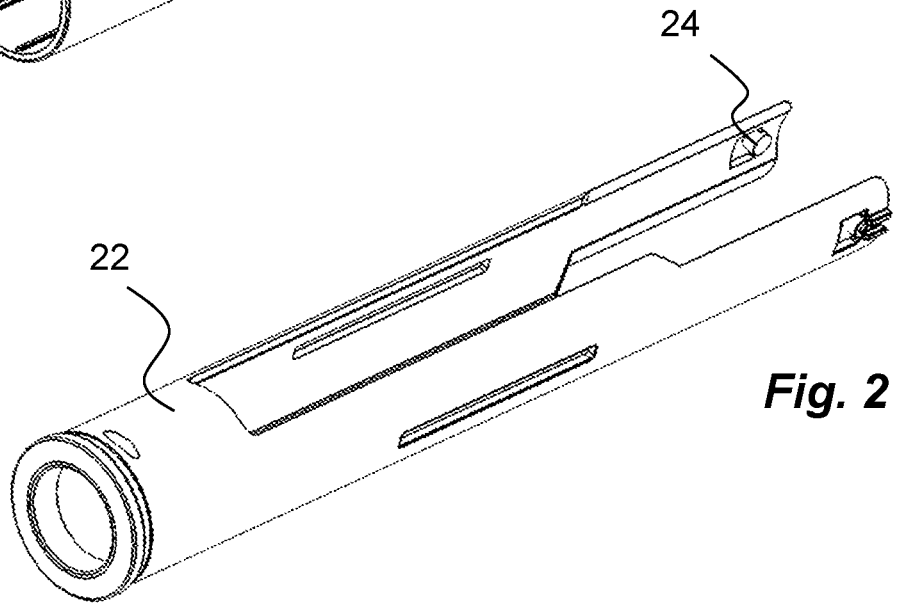

As seen in FIG. 2, the medicament delivery device may further be arranged with a tubular activation member 22 in the form of a medicament delivery member guard. The activation member 22 may be arranged with first co-acting elements 24, which in an exemplary embodiment are two protrusions, which are used for activating the medicament delivery device as will be described in detail below. According to an embodiment of the disclosure, a tension spring 25 is arranged at the proximal end of the activation member 22 for moving it in a proximal direction.

Figure 3:
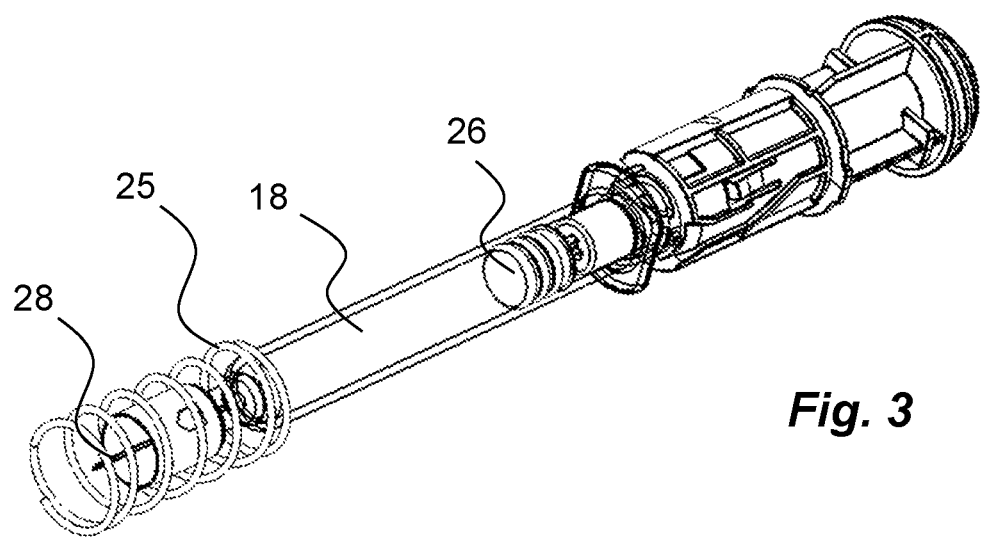
Figure 4A:
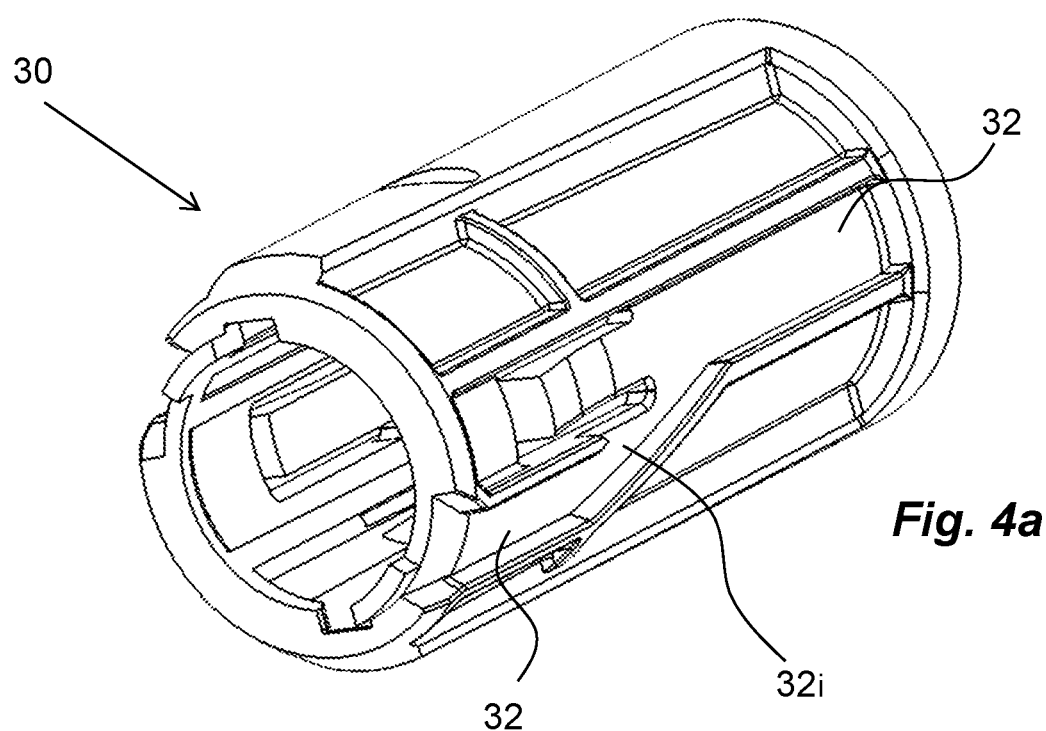

FIG. 3 illustrates the interior of the medicament delivery device. The medicament container 18 is arranged within the container holder 16 and has a predetermined volume of medicament, a slidable stopper 26 and a medicament delivery member 28. The medicament container 18 may be a syringe provided with a needle 28 as the delivery member; however the disclosure should not be limited to this. The medicament delivery device may also comprise a tubular rotator 30, FIG. 4a, comprising grooves 32 on its outer surface interactively connected to the protrusions 24 of the medicament delivery member guard 22, FIG. 2.

Figure 4B:
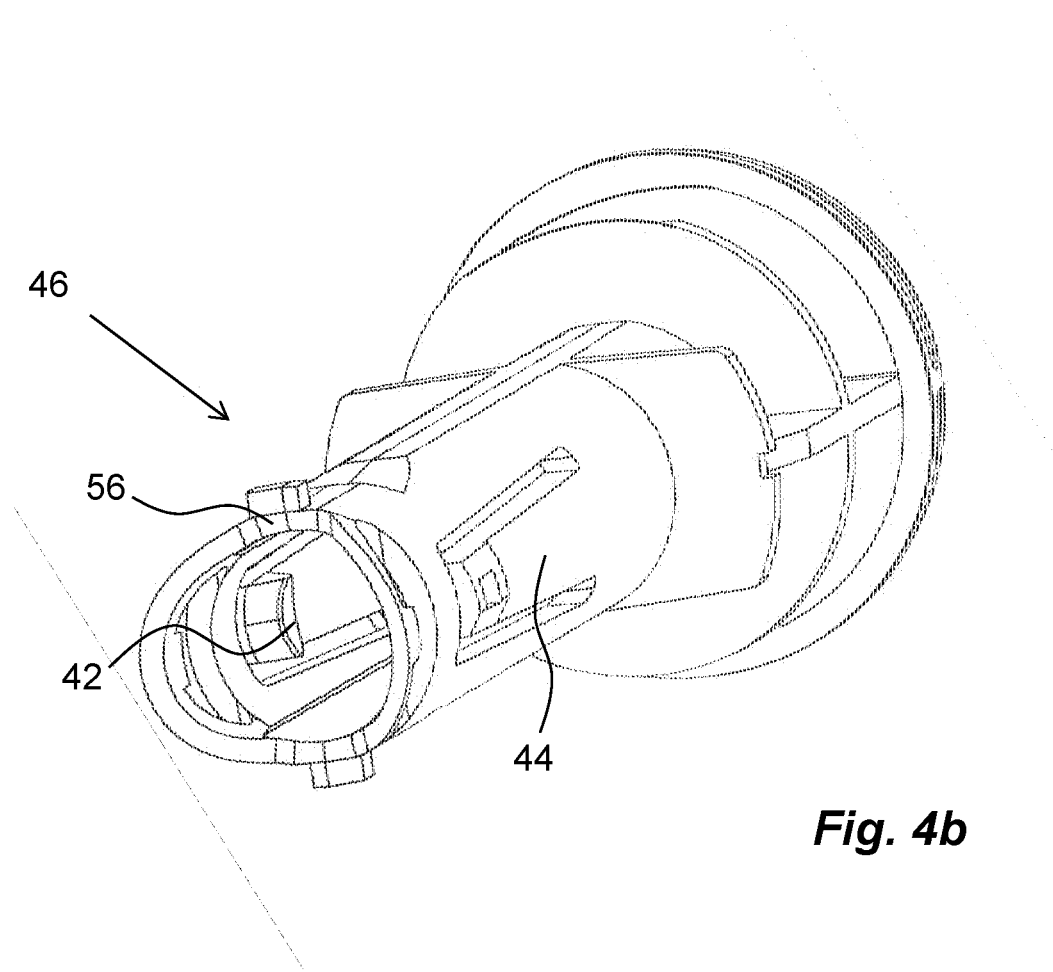
Figure 5A:
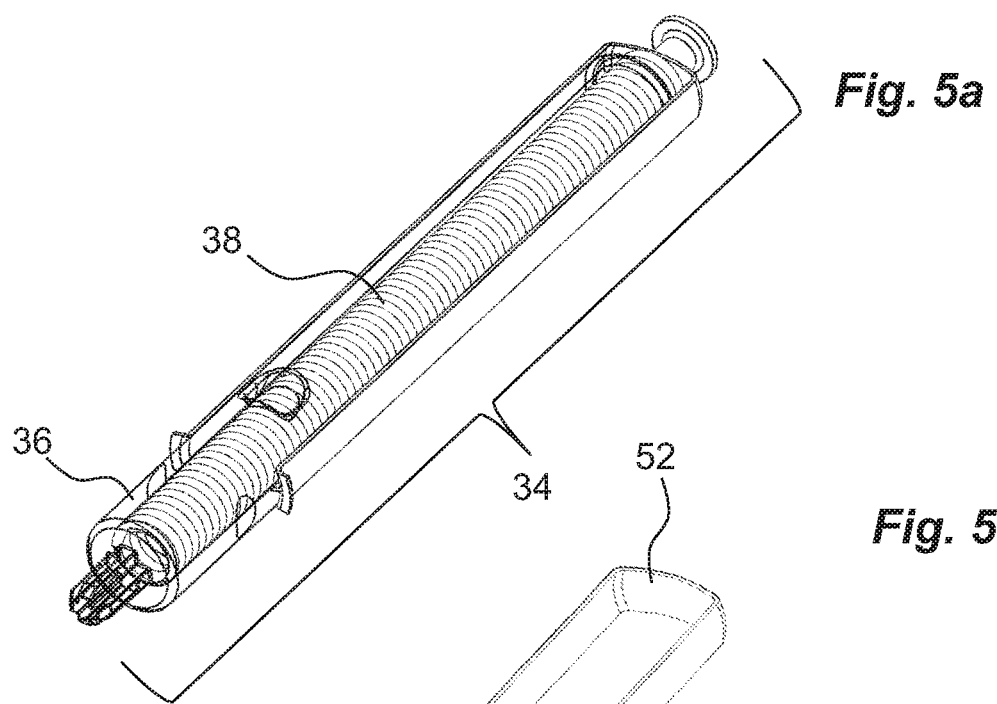
Figure 5B:
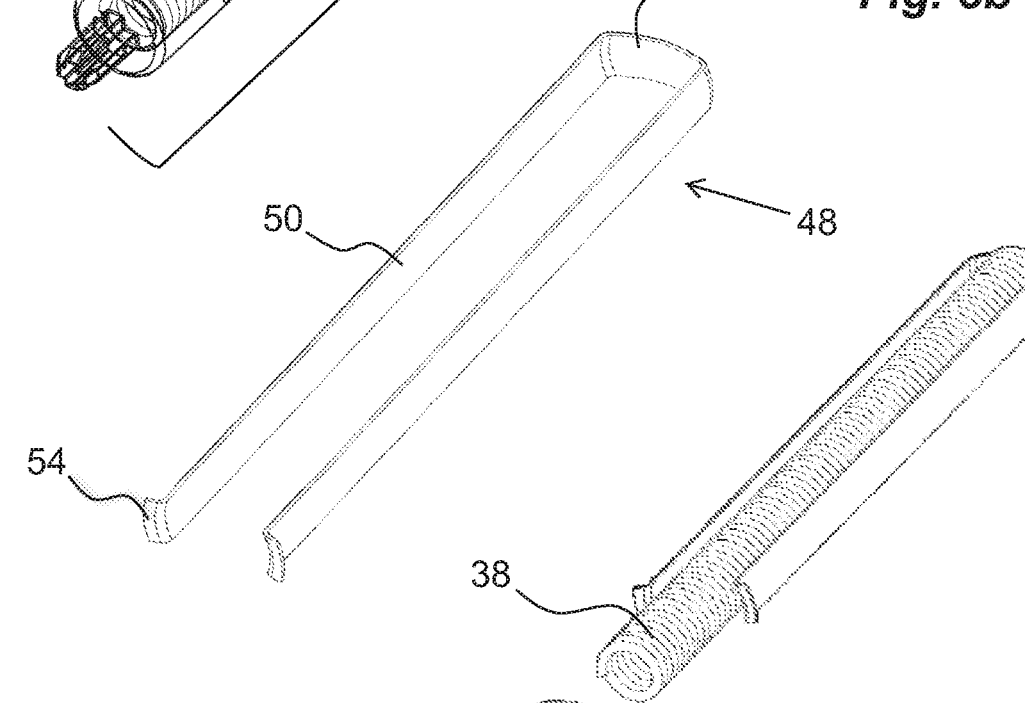
Figure 5C:
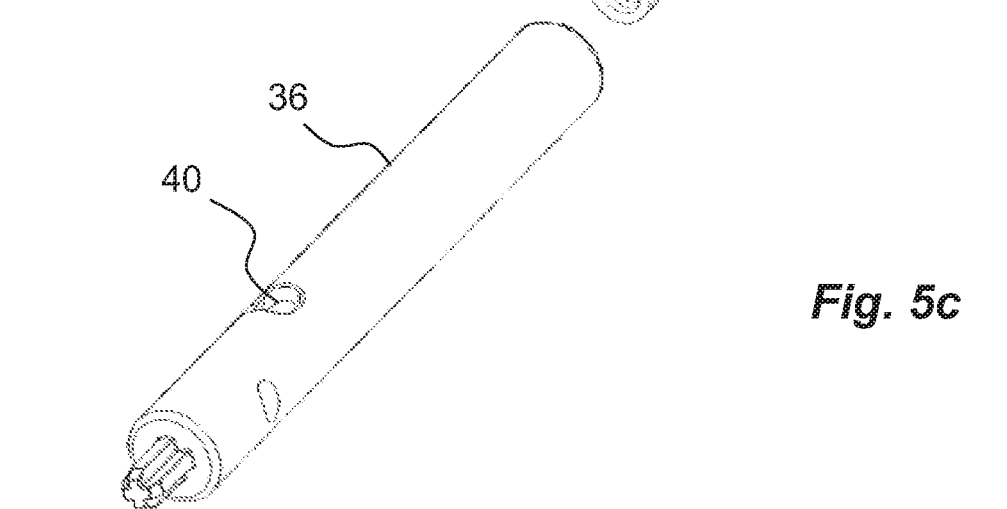

Further the medicament delivery device comprises a drive mechanism 34, FIG. 5. The drive mechanism comprises a plunger rod 36 and a compression spring 38 arranged within the plunger rod 36. The plunger rod 36 comprises a cut-out/recess 40, FIG. 5, interactively connected to inwardly directed protrusions 42 on proximally directed flexible arms 44 of an actuator 46, FIG. 4b. The proximal end of the plunger rod 36 is in contact with the slidable stopper 26, FIG. 3. The rotator 30 is rotatably and coaxially arranged around the actuator 46, acting on the flexible arms 44.

The drive mechanism 34 further comprises a switching element 48, the purpose of which will be described below. In the illustrated embodiment, the switching element 48 comprises an elongated u-shaped bracket, provided with at least two elongated arms 50, directed in the proximal direction, and a lower part 52, a distal transversal end wall, directed in the distal direction of the medicament delivery device. The switching element 48 may be made from metal, plastic, or any combination of these materials.

The proximal ends of the arms 50 of the switching element 48 are provided with angled support protrusions 54 extending in generally radially outward directions with regard to a longitudinal axis of the switching element 48. The arms 50 of the switching element 48 are arranged to extend along the length of the plunger rod 36, FIG. 5a, and the support protrusions 54 are adapted to rest on a proximally directed end surface 56 of the actuator 46, FIG. 4b, when the plunger rod 36 and the compression spring 38 are in a tensioned state, i.e. the inwardly directed protrusions 42 of the flexible tongues 44 of the actuator 46 are positioned in the recesses 40 of the plunger rod 36. When the plunger rod 36 and the compression spring 38 are in the pre-tensioned state, the distal end of the switching element 48 is arranged at a predetermined distance "D", FIG. 6a, from an inner distal surface of a switch 58, the function of which will be described in detail below.

The device is intended to function as follows. The user presses the proximal end of the device with the medicament delivery member guard 22 against a dose delivery site and when an injection needle is used as medicament delivery member 28, a penetration is performed on the user's skin. The penetration causes the housing 10 to be moved in the proximal direction in relation to the medicament delivery member guard 22. This in turn causes the protrusions 24 of the medicament delivery member guard 22 to move in the grooves 32 of the rotator 30 such that the protrusions 24 will come in contact with inclined groove sections $32_i$, which will cause the rotator 30 to turn around the longitudinal axis of the medicament delivery device.

The turning of the rotator 30 will activate the drive mechanism 34 in that the arms 44 of the actuator 46 are freed. The arms 44 may then flex outwardly, whereby the inwardly directed protrusions 42 of the arms 44 are moved out of contact with the recesses 40 of the plunger rod 36. The drive spring 38 of the plunger rod 36 now urges the plunger rod 36 in the proximal direction for expelling a dose of medicament through the medicament delivery member 28 until the stopper 26 of the medicament container 18 reaches its most proximal position.

When the stopper 26 has been moved by the plunger rod 36 to almost the proximal end inside the medicament container 18, the plunger rod 36 is moved out of contact with the arms 50 of the switching element 48 as seen in FIG. 6c. The arms 50 of the switching element 48 are thus free to flex inwards such that the support protrusions 54 are moved out of contact with the surfaces 56 of the actuator 46, and due to the force of the compression spring 38 in contact with and acting on the lower part 52 of the switching element 48, the switching element 48 will be moved suddenly in the distal direction the distance D until the distal end of the switching element 48 hits the switch 58, thereby activating the switch 58, FIG. 6c. The activation of the switch will in turn activate a communication unit 60, i.e. powering the communication unit. The function of the communication unit will be described in detail below.

Figure 8B:
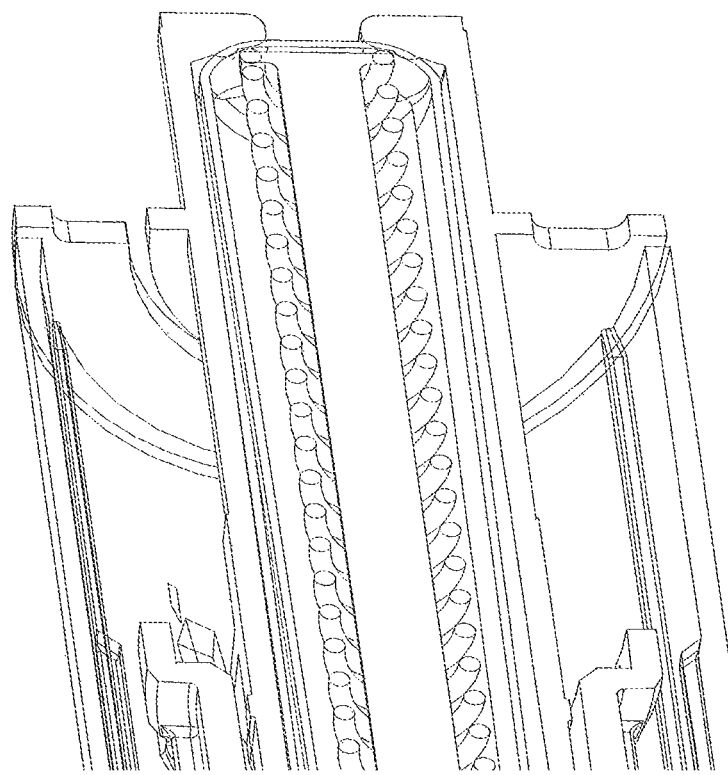
FIG. 8 shows the embodiment of FIG. 7 in a closed position.
Figure 8A:
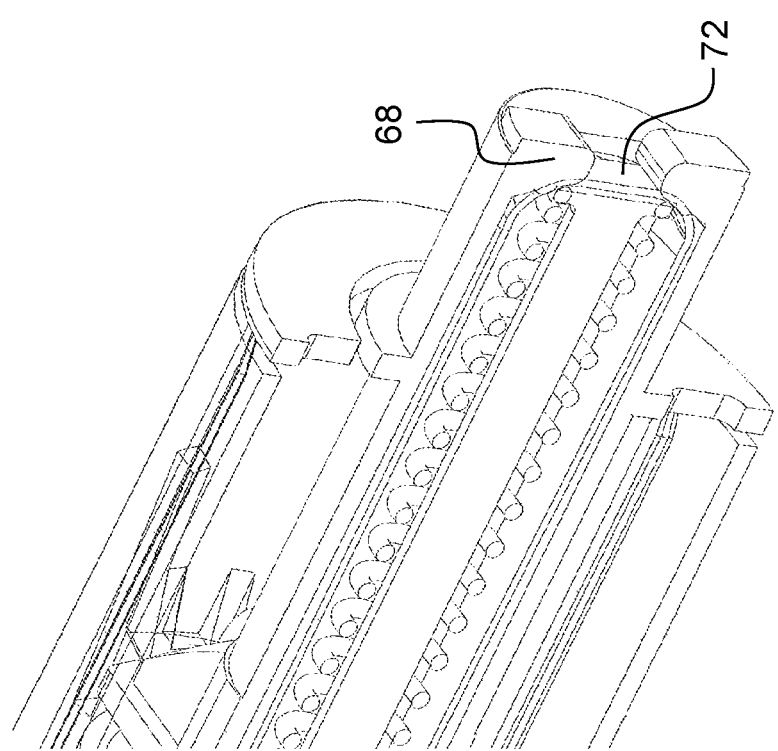

It is to be understood that the switch may have a number of different designs depending on the type of device and its operating components as well as the kind of signal that is to be obtained. FIGS. 7 and 8 show one type of switch that can be used with the switching element described in connection with the above embodiment.

Here a distal end of the actuator 46 is arranged with an end wall 62, provided with a generally rectangular cut-out 64. On opposite sides of the cut-out, two proximally directed, somewhat inclined, contact surfaces 66 are arranged, which surfaces the switching element 48 will hit when released. The inclined contact surfaces are provided with conductive material. The conductive material extends through the cut-out 64 as leads 68, wherein suitable conduits 70, FIG. 6c, are connected to these leads 68 and then extend to the communication unit 60. Further, the switching element 48 may be made of metal, such that when the switching element 48 is moved in contact with the contact surfaces 66, the switch is closed. As an alternative the distal end surface 72 of the switching element may also be covered with conductive material. The contact surfaces 66 may further be arranged with protrusions 74, FIG. 7b, in order to enhance the contact reliability between the switching element 48 and the contact surfaces 66. FIG. 8 show when the switching element is moved in contact with the contact surfaces.

Figure 10B:
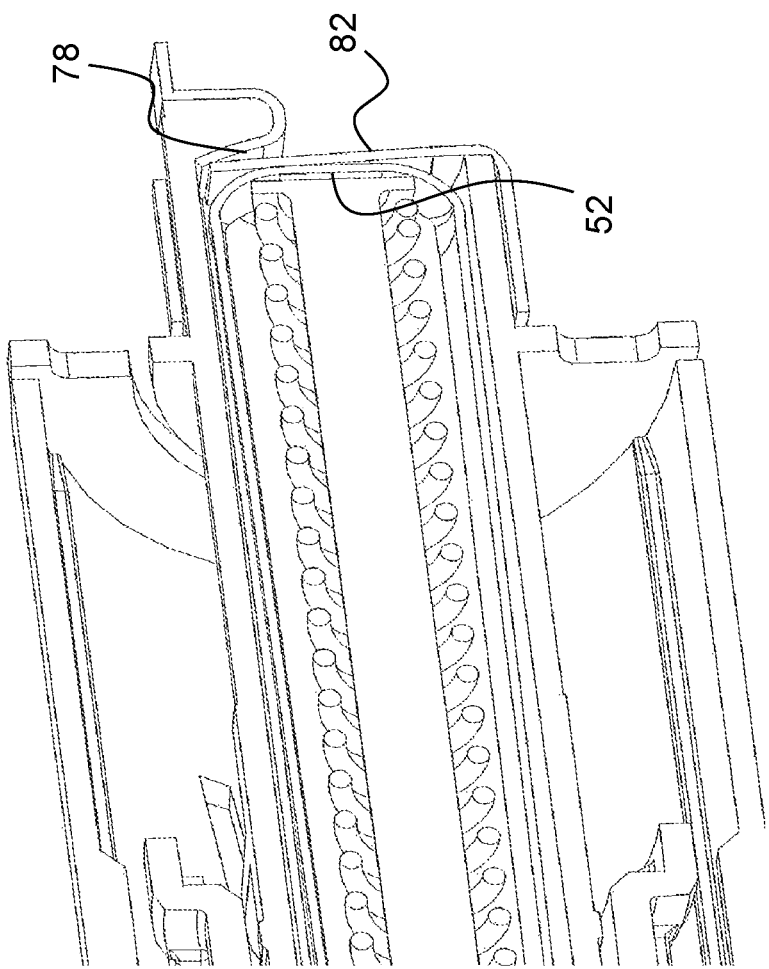
FIG. 10 shows the embodiment of FIG. 9 in a closed position.
Figure 10A:
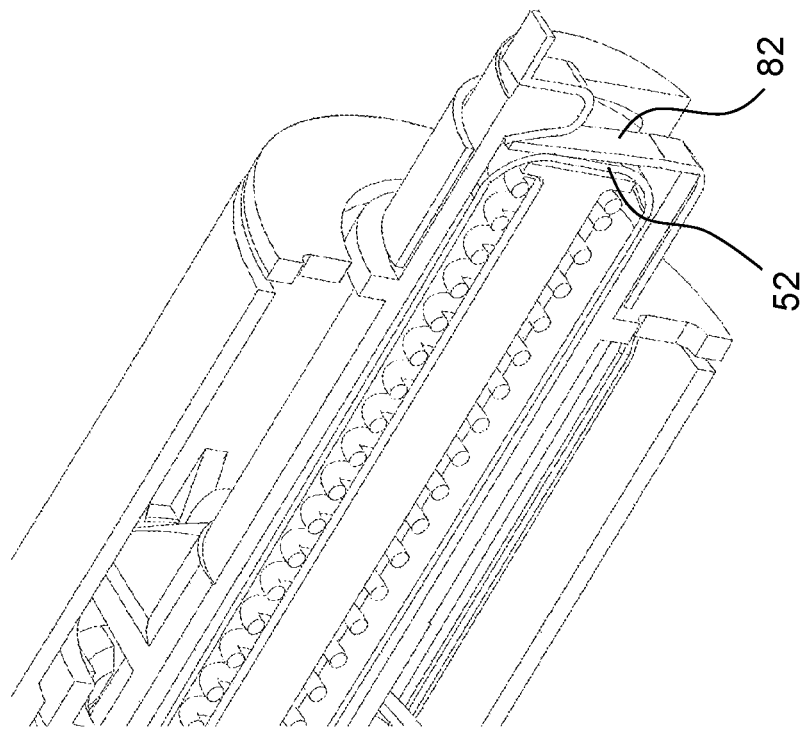

FIGS. 9 and 10 display another embodiment of a switch to be used with the medicament delivery device described above. Also here, the actuator is arranged with an end wall 62 at its distal end. The end wall 62 is arranged with a generally rectangular cut-out 76. One proximally directed, somewhat inclined, contact surface 78 is arranged adjacent one edge of the cut-out. The contact surface 78 is arranged with conductive material, which extends through the cut-out as a lead 79, wherein a suitable conduit 70 is connected to this lead, which conduit is connected to the communication unit 60. Further, a contact element is arranged. It comprises a tongue 82 of a flexible material extending into the interior of the actuator with an inclination a in relation to a normal of the longitudinal axis L of the medicament delivery device when in unaffected, initial, position. Further, in the unaffected, initial, position there is a certain gap between the free end of the tongue 82 and the contact surface 78. Even though the tongue 82 is arranged to be flexible it is understood that it should be so rigid that the tongue 82 cannot be moved in contact with the contact surface if the medicament delivery device is dropped on the floor for instance.

The tongue 82 is attached to, or made integral with, a generally tubular seat 84 surrounding a distal part of the actuator 46. The seat 84 is further arranged with conductive material and is connected to the communication unit 60 via a suitable conduit 70. When the switching element 48 pushes on the tongue 82 in the distal direction with its lower part 52, whereby the tongue 82 is moved in contact with the contact surface 78 and the switch 60 is closed, as seen in FIG. 10. In this embodiment, the switching element 48 may be of any suitable material; it does not have to be made of metal.

Regarding the contact surfaces and the leads of the embodiments described above, they can be created in many ways. They can be made by thin conductive sheet material that is bonded to components in suitable ways, such as gluing. As an alternative, the Laser Direct Structuring (LDS) technology may be utilized in creating conductive surfaces on different components. In this regard, the switching element of the first switch embodiment may be of a non-conductive material, where the distally directed end surface is treated with a conductive material, for instance with LDS.

FIGS. 11-15 disclose a second embodiment of a medicament delivery device comprising the present disclosure. The embodiment shown in the drawings comprises a generally elongated main housing 100 having a distal end 102 and a proximal end 104, FIG. 11.

Figure 14:
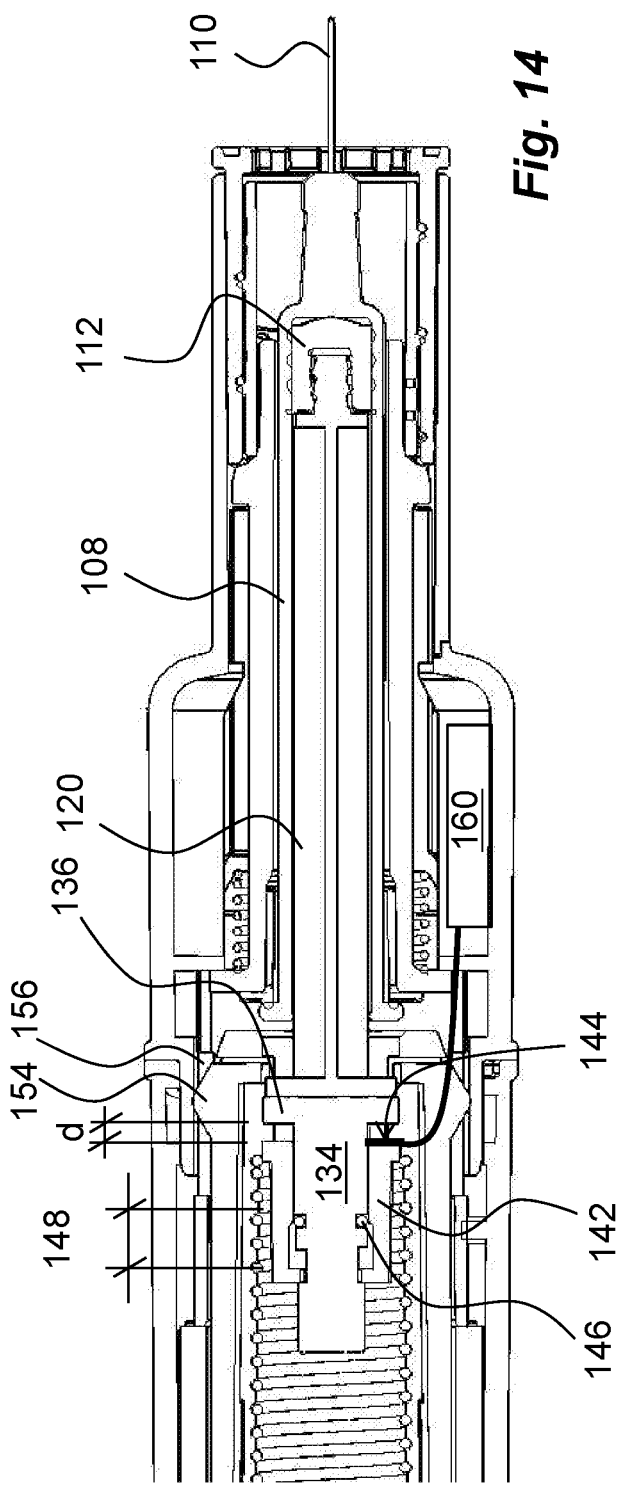

The housing 100 is designed to accommodate a medicament container 108, FIG. 14. An appropriate medicament delivery member 110, FIG. 14, is attached to, or made integral with, the medicament container 108. A movable stopper 112 is further arranged inside the medicament container, FIG. 14.

Figure 11:
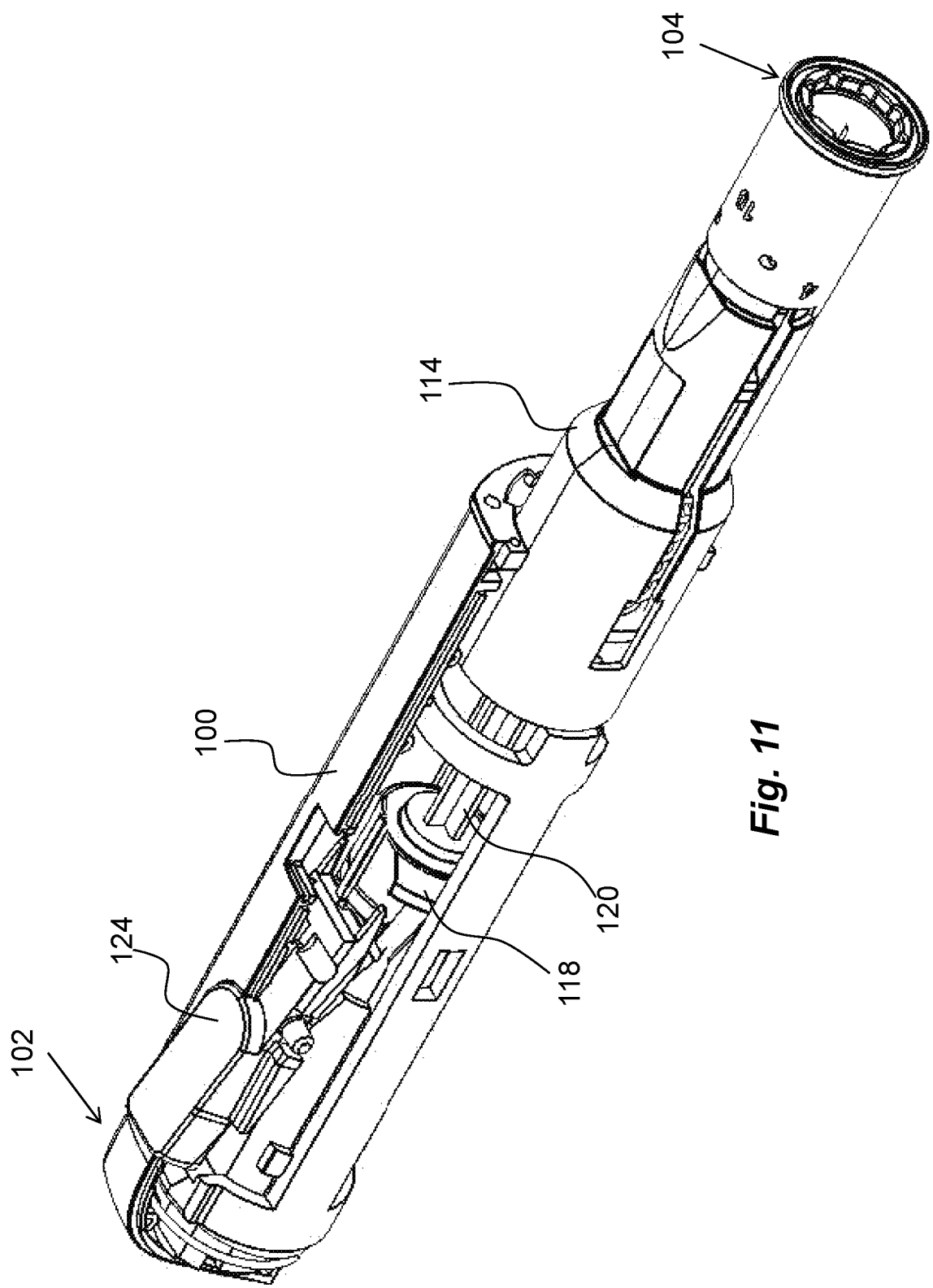
FIG. 11 shows a perspective view partly dis-assembled of a second embodiment of a medicament delivery device comprising a communication unit.

Surrounding the medicament container 108 and coaxial therewith is a medicament delivery member shield 114, FIG. 11. The medicament delivery member shield 114 can move in the longitudinal direction in relation to the housing 100.

Figure 13:
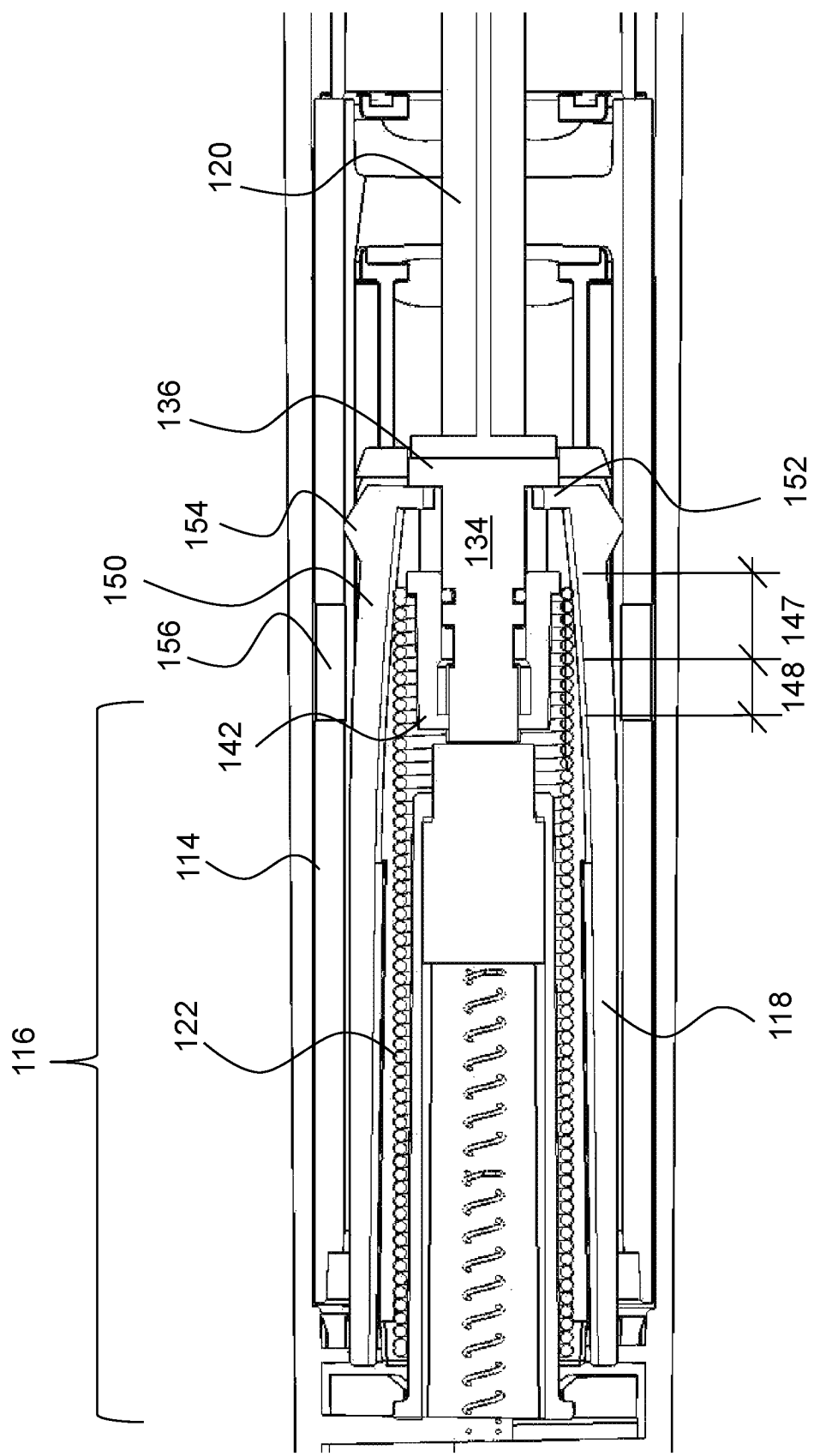

The device further comprises a drive mechanism 116, FIG. 13. The drive mechanism 116 comprises a plunger rod driver 118 arranged axially moveable within the housing 100. The proximal end of the plunger rod driver 118 is operably connected to a distal end of an elongated plunger rod 120, FIG. 11.

The drive mechanism 116 further comprises a drive spring 122, here in the form of a helical coil spring, FIG. 13, which biases the plunger rod driver 118 towards its proximal end position. A manually operated release button 124, for releasing the plunger rod driver 118 of the drive mechanism 116 from the distal, or cocked, position to the proximal, or extended, position is arranged extending through the housing 100, FIG. 11. The release button 124 is operably connected to a drive mechanism locking element 126 which locks and interworks with the plunger rod driver 118 via a proximally directed ledge 128 positioned in a groove 130 to hold the plunger rod driver 118 with the drive spring 122 in the tensioned state.

According to the second embodiment, the drive mechanism 116 is arranged with a switching mechanism. It comprises a switching element 132, FIG. 12, comprising an elongated tubular body 134, provided with a circular end plate 136 with a proximally directed end surface, which is intended to be in contact with a distally directed end surface of the plunger rod 120. Further, the side surface of the body 134 of the switching element 132 is arranged with a circumferential groove 138, FIG. 12. The body 134 is arranged to fit into a central passage 140 of a tubular element 142 attached to a proximal area of the plunger rod driver 118, FIG. 13.

Figure 12:
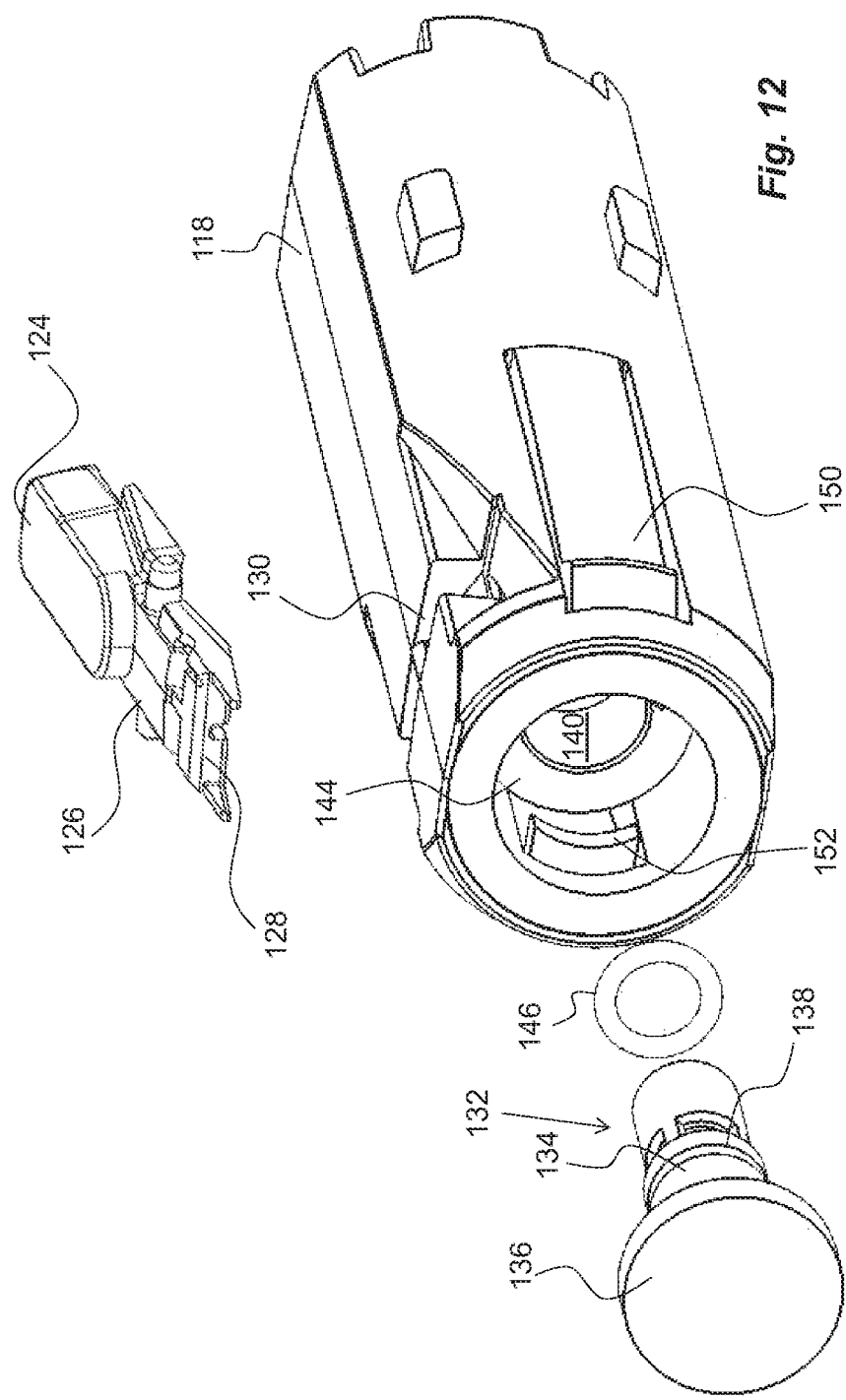
FIGS. 12 to 15 show different detailed views of the embodiment of FIG. 7.
Figure 29:
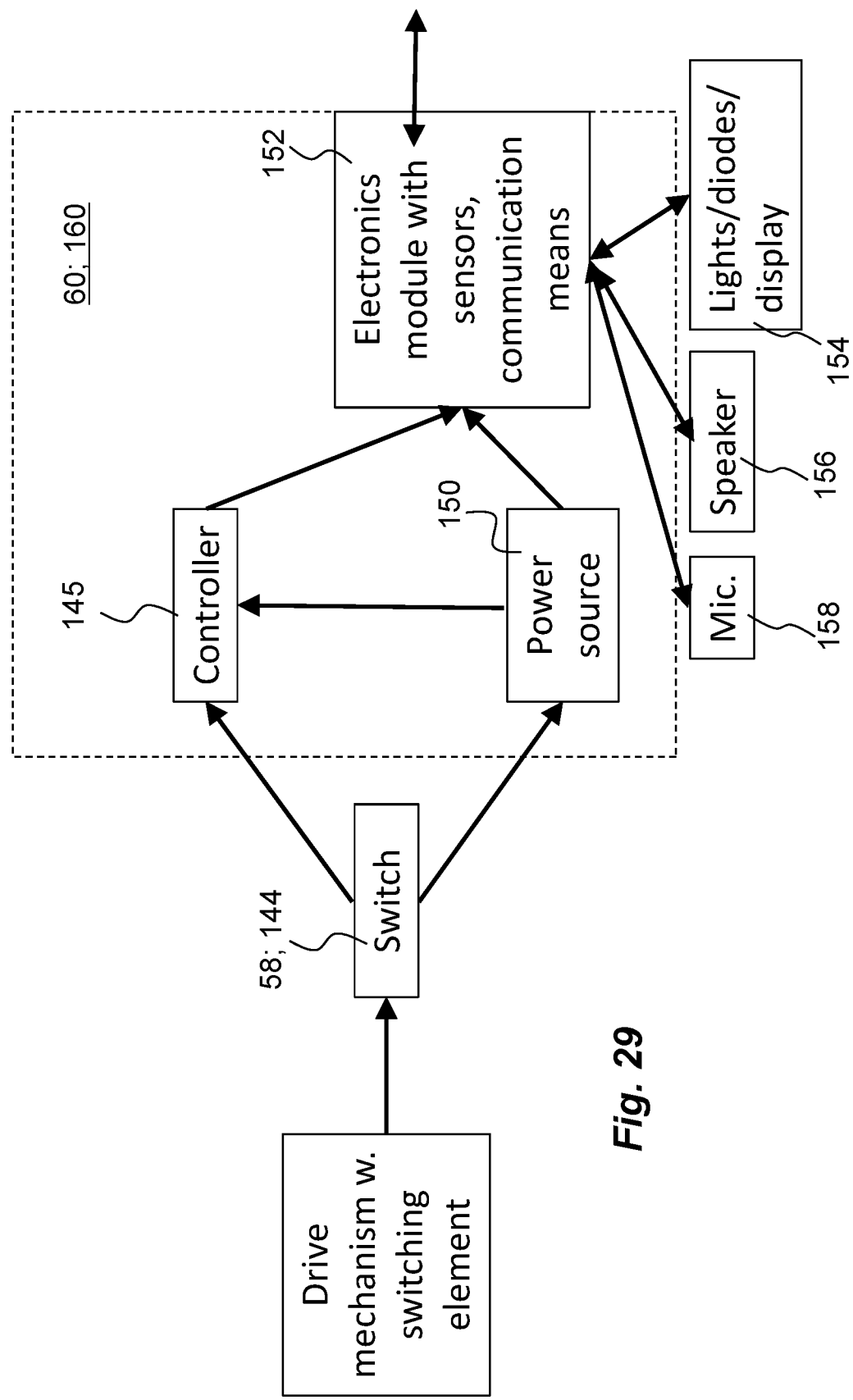
FIG. 29 shows a communication unit according to the disclosure.

The tubular element 142 is arranged with a proximally directed annular switch 144 at the proximal end of the plunger rod driver 118, FIG. 12. The switch can be of many different configurations and designs. For example, the switch may be a piezo-electric element capable of providing an electric signal when mechanically affected. Further, the switch 144 can also be a mechanical contact having electric contact points that are brought in contact when the switch is mechanically affected as will be explained below. The switch 144 is further connected to a microcontroller 145 of a communication unit 160 of the medicament delivery device, FIG. 29, arranged to perform a number of functions as will be described.

The area of the plunger rod driver 118 proximal of the switching element 132 has a diameter somewhat larger than the diameter of the end plate 136, such that the latter may fit into the proximal end of the plunger rod driver 118, as seen in FIG. 12.

Preferably the device is arranged with a switching delay mechanism. It comprises a friction enhancing element 146 intended to fit into the circumferential groove 138 of the switching element 132. In the embodiment shown the friction enhancing element 146 is an O-ring made of a resilient material such as rubber. The central passage 140 of the tubular element 142 is arranged with a first section 147, FIG. 13, having a diameter somewhat smaller than the diameter of the O-ring when fitted into the circumferential groove such that the O-ring is compressed when placed in the first section 147. The central passage is further arranged with a second section 148, FIG. 13, which has a diameter that is slightly larger than the diameter of the O-ring, the function of which will be described below.

Further, a switching mechanism for the release mechanism is provided on the plunger rod driver 118. It comprises two arms 150, FIG. 13, attached to the plunger rod driver 118 and extending in the proximal direction, where the arms 150 are positioned on opposite sides of the central passage 140. Each arm 150 is arranged with a generally radially inwardly directed ledge 152. The inwardly directed ledges 152 are arranged to extend into the central passage 140. Further the arms 150 are arranged with generally radially outwardly extending ledges 154, the function of which will be described below.

This second embodiment is intended to function as follows. When to be used, the proximal end of the medicament delivery device is pressed against a dose delivery site. The user depresses the trigger button 124, whereby the drive spring 122 is released. The plunger rod driver 118 and the drive spring 122 then acts to force the plunger rod 120 in the proximal direction acting on the stopper 112 inside the medicament container 108. Since the medicament is incompressible and the passage through the medicament delivery member 110 is narrow, the medicament container 108 will be moved in the proximal direction. The movement of the medicament container 108 will now cause a penetration of the medicament delivery member 110 into the skin of the user.

The force of the drive spring 122 now forces the plunger rod 120 in the proximal direction in relation to the medicament container 108, moving the stopper 112 in the proximal direction, whereby a dose of medicament is delivered into the body of the user, FIG. 14. When the plunger rod 120 is moving in the proximal direction, so is the switching element 132. This is due to the arms 150 being forced radially inwards due to the outwardly directed ledges 154 being in contact with an inner surface of the medicament delivery member guard 114 as seen in FIG. 12. The inwardly directed ledges 152 of the arms 150 are then abutting a distally directed surface of the end plate 136 of the switching element 132.

When the plunger rod driver 118, the switching element 132, the plunger rod 120 and the stopper 112 have reached a position close to the proximal end position of the stopper 112, the outwardly directed ledges 154 of the arms 150 will enter cut-outs 156 of the medicament delivery member shield 114, FIGS. 13 and 14. The arms 150 are then free to move radially outwardly when the outwardly directed ledges 154 enter the cut-outs 156. Thereby, the inwardly directed ledges 152 will be moved out of contact with the end plate 136 of the switching element 132.

The force of the drive spring 122 will continue to urge the plunger rod driver 118 in the proximal direction in relation to the switching element 132. However, the relative movement between the plunger rod driver 118 and the switching element 132 is slowed due to the friction enhancing element 146 frictionally acting on the inner surface of the tubular element 142 of the plunger rod driver 118. The friction also aids in transferring some force to the plunger rod 120, ending the injection sequence.

Figure 15:
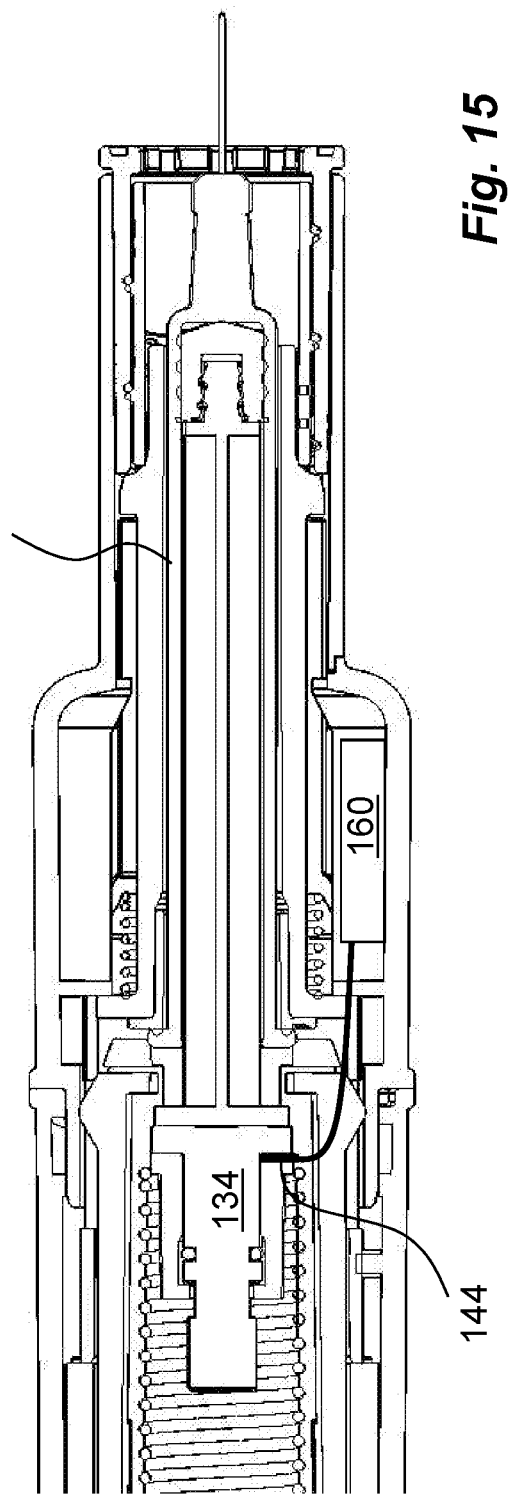

The relative movement continues between the plunger rod driver 118 and the switching element 132. When the friction enhancing element 146 has been moved along the first section 147 it reaches the second section 148, as seen in FIG. 14. Now the friction enhancing element 132 is moved out of contact with the inner surface of the tubular element 142. As seen, the distally directed surface of the end plate 136, is positioned a distance d from the switch 144 as seen in FIG. 14. The force from the spring 122 still acts on the plunger rod driver 118 and since it now can move freely, it will accelerate in the proximal direction the distance d until the distally directed surface of the end plate 136 comes in contact with the switch 144, as seen in FIG. 15. The switch then activates the communication unit 160 of the medicament delivery device.

FIGS. 16-24 show a third embodiment of a medicament delivery device. The embodiment, FIG. 16, comprises a generally elongated medicament delivery device 210 comprising the present disclosure and having a distal end 212 and a proximal end 214. The medicament delivery device 210 is provided with an elongated housing, comprising a proximal housing part 216 and a distal housing part 218. The distal end of the proximal housing part 216 is arranged with attachment elements 219 such as annular recesses e.g., FIG. 17a, on its inner surface adapted to interface with corresponding attachment elements 220, FIG. 16, on e.g. the proximal outer surface of the distal housing part 218. The distal housing part 218 is further arranged with a central wall 222, FIG. 20, which wall 222 is provided with a central passage 223. The passage 223 is further arranged with a distally directed annular ledge 225.

Figure 16:
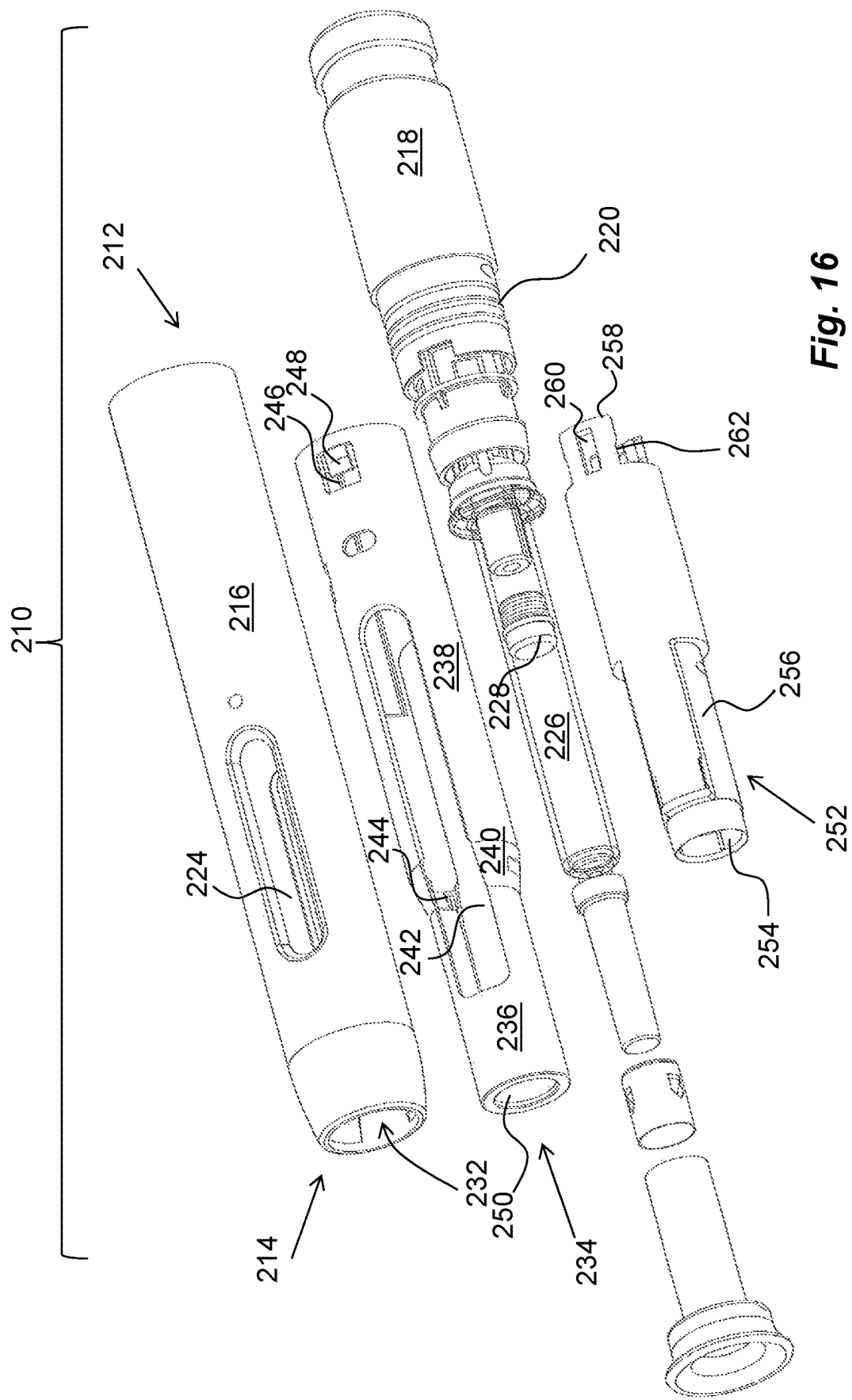
FIG. 16 shows a third embodiment of a medicament delivery device comprising a communication unit.

The proximal housing part 216 is arranged with elongated openings 224 for viewing a medicament container 226, FIG. 16. The medicament container 226 is arranged with a movable stopper 228 and a medicament delivery member 230, FIG. 17a. In the embodiment shown, the medicament delivery member 230 is integrated in the medicament container 226 as seen in FIG. 17a, but it is to be understood that the medicament delivery member 230 may be an attachable member wherein the attachment elements may be threads, bayonet fittings or luer-couplings, just to mention a few.

The proximal housing part 216 is further arranged with a central passage 232 through which a medicament delivery member guard 234 can extend. The medicament delivery guard 234 comprises a first proximal part 236 having a certain diameter and a second distal part 238 having a diameter larger than the proximal part, where these parts are joined by an intermediate conical part 240, FIG. 16. Two elongated slits 242 are arranged along the medicament delivery member guard 234, on opposite sides thereof, for viewing the medicament container 226. On an inner surface of the conical part 240 a ledge 244 is arranged.

Further, at the distal end of the medicament delivery member guard 234 two openings 246 are arranged opposite each other, where each opening 246 is arranged with somewhat inwardly projecting, flexible, tongues 248, FIG. 16. The medicament delivery member guard 234 is further arranged with a central opening 250 at its proximal end, through which the medicament delivery member 230 may protrude as will be described.

A generally tubular medicament container holder 252 is slidably and coaxially arranged inside the medicament delivery member guard 234. The proximal part of the medicament container holder 252 is arranged with a neck portion 254 of lesser diameter. Adjacent the neck portion 254 cut-outs have been made on either side to form guide surfaces 256. These guide surfaces 256 cooperate with corresponding shapes of the inner surface of the medicament delivery member guard 234 in order to obtain a stop mechanism against rotation of the medicament container holder 252 relative the medicament delivery member guard 234. The distal end of the medicament container holder 252 is arranged with two distally extending tongues 258, where each tongue is arranged with an opening 260 and an inwardly directed ledge 262 on the distal edge of each opening, FIG. 16.

Figure 18:
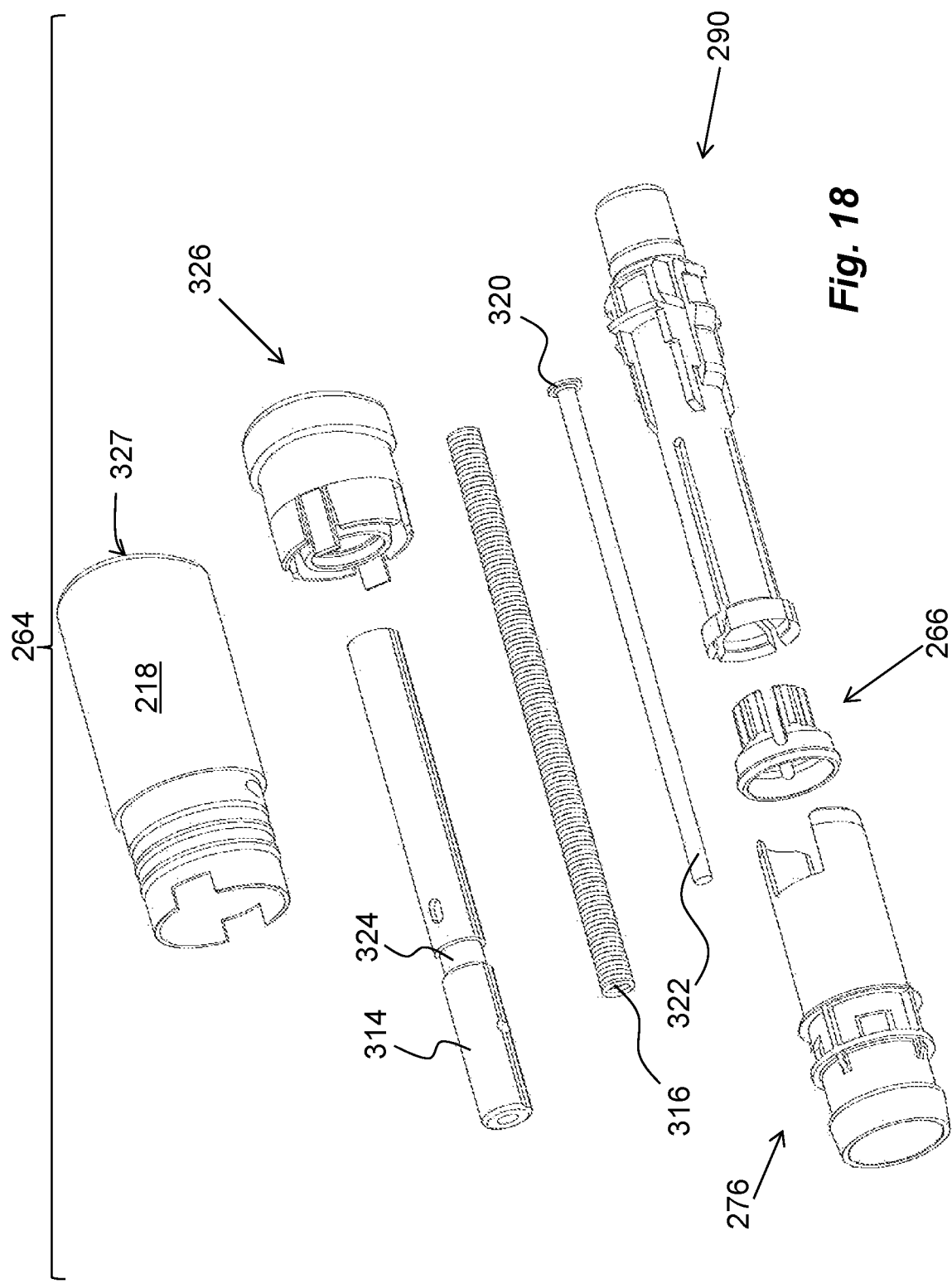
FIG. 18 shows an exploded view of a power unit comprised in the medicament delivery device of FIG. 16, FIGS. 19-20 show detailed views of components comprised in the power unit of FIG. 18, FIGS. 21-22 show exploded views of an activator unit comprised in the medicament delivery device of FIG. 16, FIGS. 23-28 show different functional views of the medicament delivery device of FIG. 16
Figure 19:
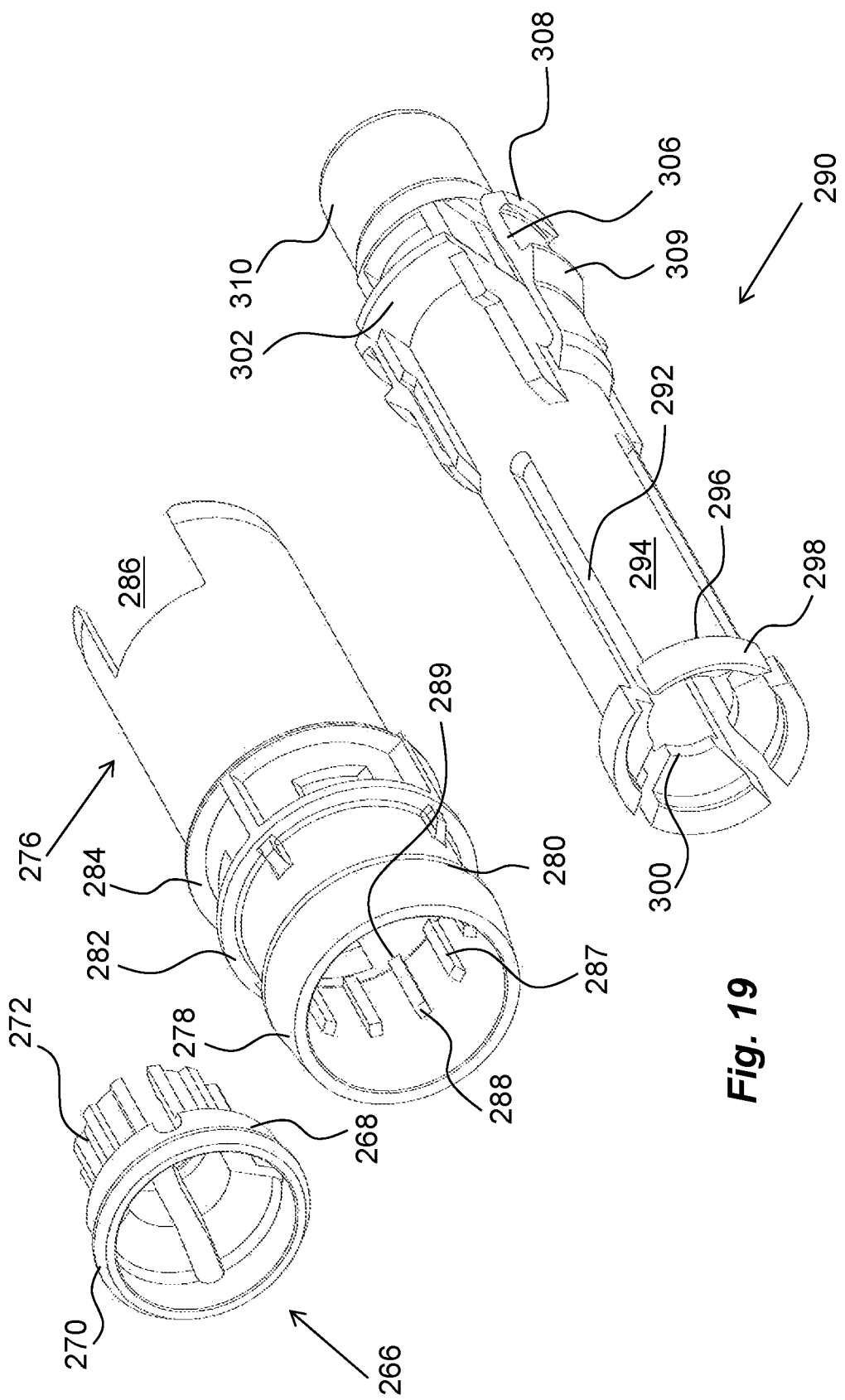
Figure 20:
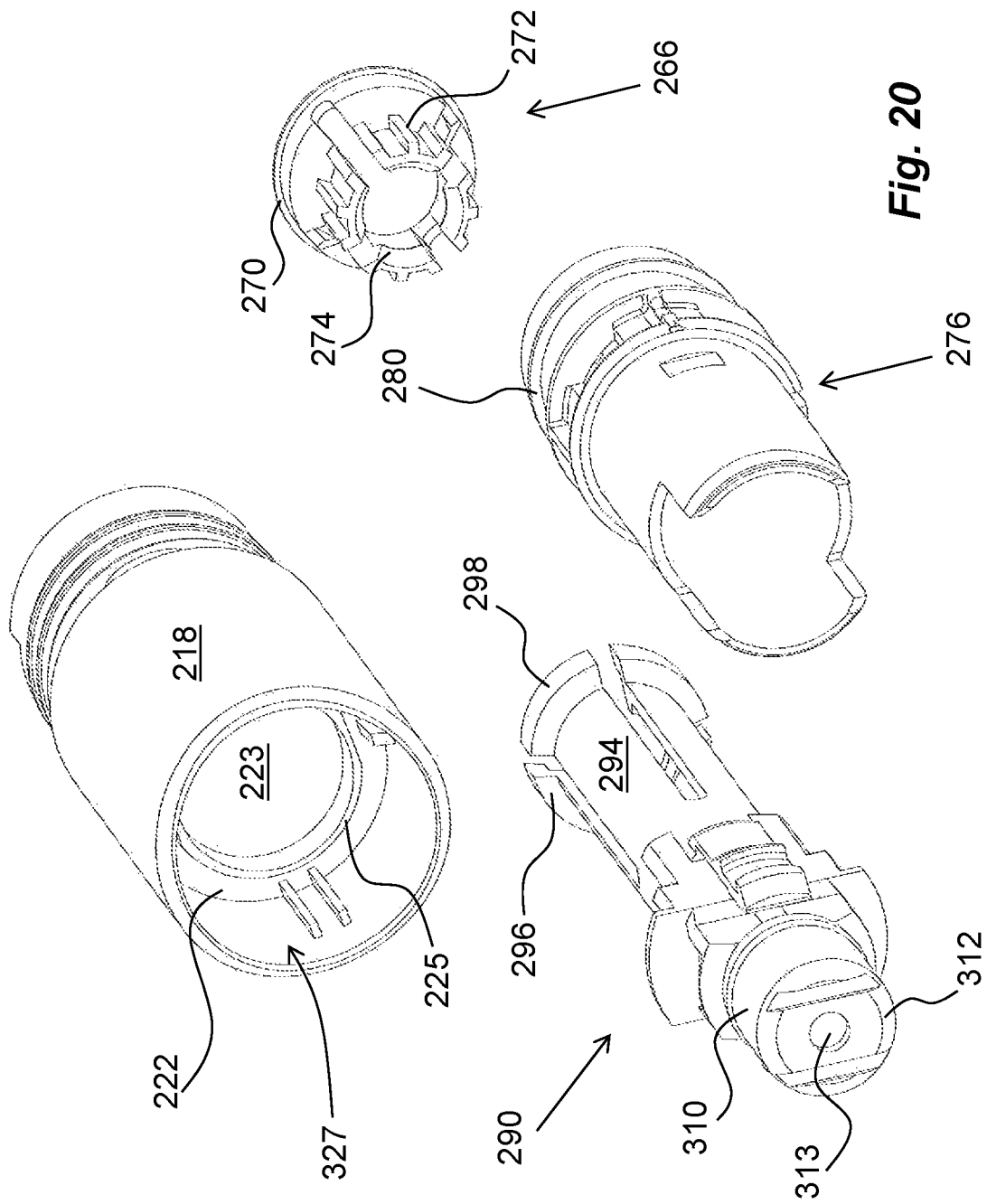

The medicament delivery device is provided with a power unit 264, FIGS. 18-20. The power unit 264 comprises a holding element 266. It comprises a ring-shaped body 268, FIG. 19, having an annular, distally directed, ledge 270 arranged around its circumference and a number of flexible tongues 272 directed towards the distal end of the device and wherein each tongue 272 is arranged with radial inwardly directed ledges 274, FIG. 20. The holding element 266 is intended to interact with the container holder 252 as will be described below. The power unit 264 further comprises an actuator sleeve 276 which is slidably and coaxially arranged to the housing and connected to the medicament delivery member guard 234 as will be described below.

The actuator sleeve 276 has a tubular shape and comprises a proximal end with a conical part 278 ending in a distally directed ledge 280 on its outer surface. At a distance from the ledge 280, a first annular ring 282 is arranged on the outer surface. A second annular ring 284 is also arranged a further distance from the ledge 280. The distal end of the actuator sleeve 276 is arranged with at least two oppositely arranged cut-outs 286 of a generally rectangular shape. Longitudinal extending ribs 287 are arranged on the inner surface of the actuator sleeve 276 wherein proximally directed surfaces 288 of the ribs 287 form proximally directed ledges. Also distally directed surfaces 289 of the ribs 287 form distally directed ledges, FIG. 19.

A generally tubular actuator 290, FIGS. 19 and 20, is slidaby and coaxially arranged to the actuator sleeve 276. The actuator 290 comprises a number of longitudinally directed cut-outs 292 that are arranged at the proximal end of the actuator 290 so as to form flexible tongues 294. The proximal end of each flexible tongue 294 has an inclined transition surface 296 which meets with a band-shaped part 298 with enlarged diameter. On the inner surface adjacent the transition surface 296 an annular inwardly directed ledge 300 is arranged. The tongues 294 with the ledges 300 form holding elements as will be described.

The actuator 290 is also provided with two oppositely arranged stop elements 302 directed radially outwards from the outer surface on either side in the form of proximally directed ledges, where the widths of the stop elements 302 correspond to the width of the first cut-outs 286 of the actuator sleeve 276, FIG. 19. Further, the distal area of the actuator 290 is arranged with distally directed, generally radially flexible, arms 306, where the free ends of the arms are arranged with outwardly directed ledges 308. Also, outwardly directed, wedge-shaped protrusions 309 are arranged between the attachment point of the arms 306 and the ledges 308. The actuator 290 is arranged with a distal, tubular end 310 provided with an end wall 312, which end wall is arranged with a central passage 313, as seen in FIG. 20. A medicament delivery member guard spring 315, FIG. 17a, is arranged between the second annular ring 284 and the stop elements 302, the function of which will be describe below.

The power unit 264 further comprises a plunger rod 314, FIG. 18, arranged to act on the stopper 228 of the medicament container 226. A drive spring that in the embodiment shown is a compression spring 316 is arranged inside the plunger rod 314 between a proximal wall 318 of the plunger rod 314, FIG. 17b, and a proximally directed surface of a support element 320 in the form of a plate at a distal end of a spring guide rod 322, FIGS. 17b and 18. The plunger rod 314 is arranged with a number of recesses that in the embodiment shown is an annular groove 324 with a certain width, in which annular groove 324 the annular inwardly directed ledge 300 of the actuator 290 and the radial inwardly directed ledges 274 of the holding element 266 fit, FIG. 17a. It is to be understood that the annular groove 324 may be replaced with a number of discrete recesses or cut-outs.

Figure 21:
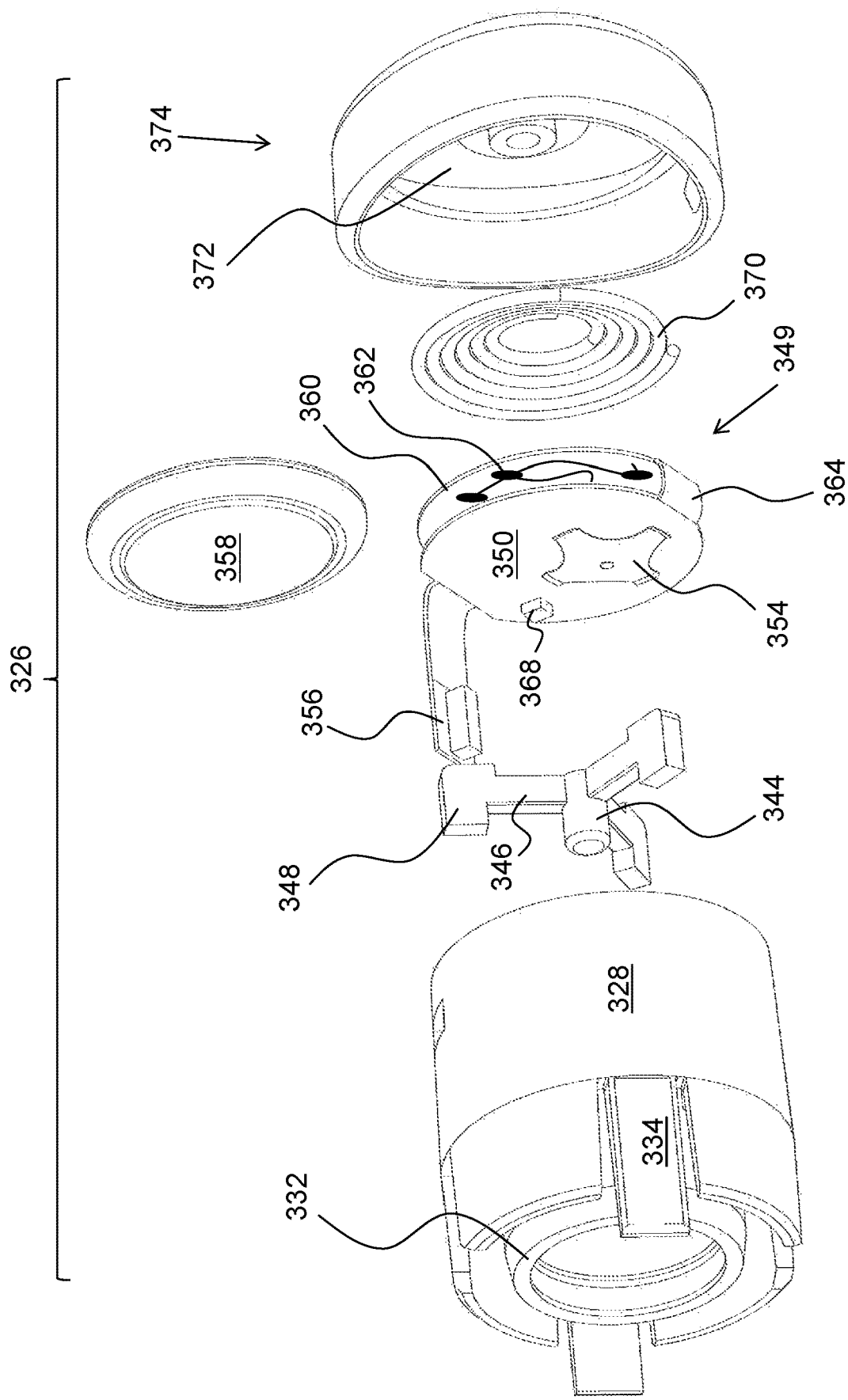
Figure 22:
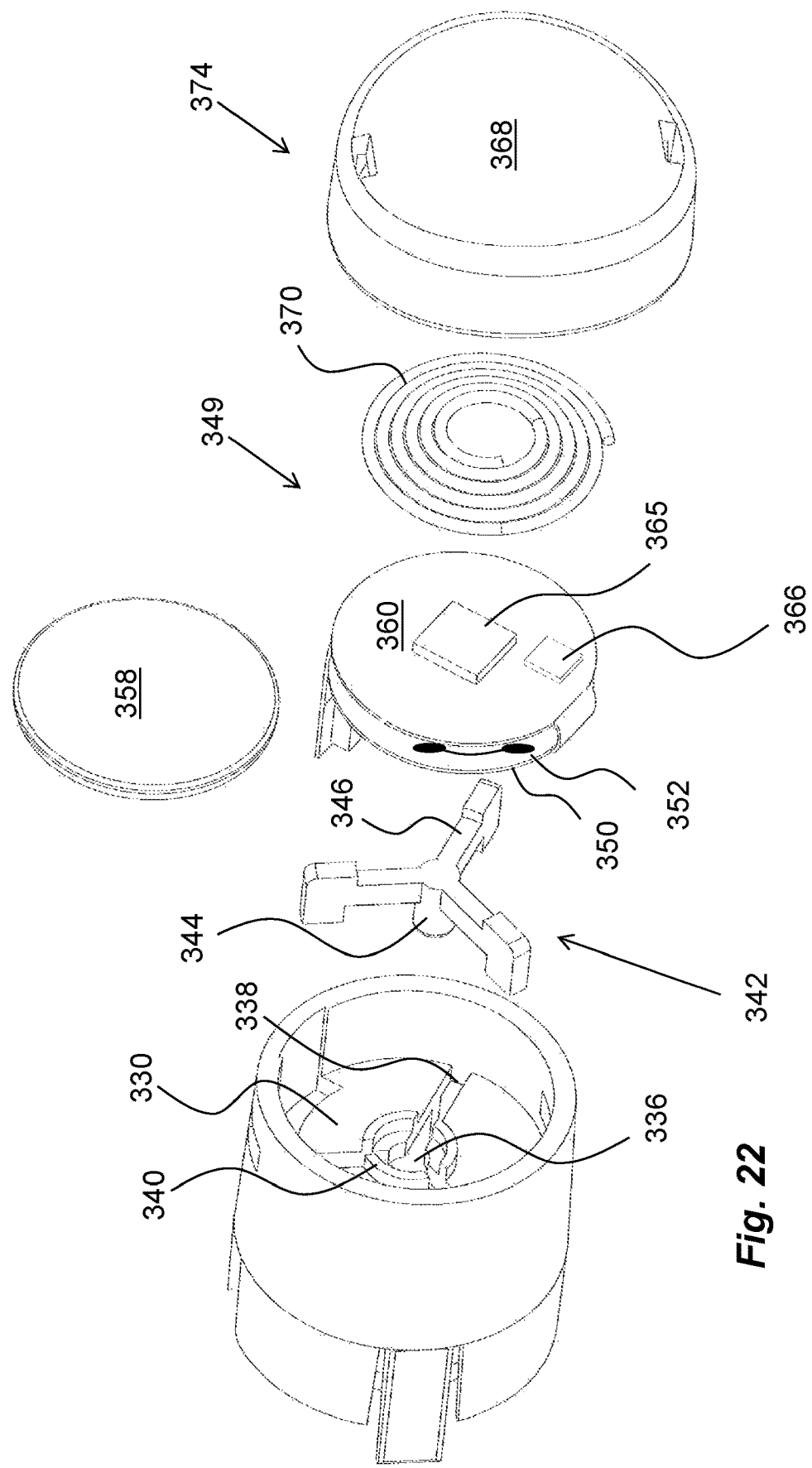

The medicament delivery device further comprises an activator unit 326, FIGS. 18, 21 and 22, that in the embodiment shown is designed as a push button extending through a distal end 327 of the distal housing part 218. The activator unit 326 comprises a generally tubular body 328 having a transversal wall 330 in its interior, FIG. 22. The proximally directed surface of the transversal wall 330 is arranged with a tubular element 332, FIGS. 17a and 21, that has a design and dimension as to fit on the distal end 310 of the actuator 290. Further the tubular body 328 is arranged with proximally directed arms 334, the function of which will be described below. The transversal wall 330 is further arranged with a central passage 336, FIG. 22, and three slits 338 extending from the central passage 336 to the interior side walls of the tubular body 328. The three slits 338 have equal angles between them. Further the distally directed surface of the transversal wall 330 is arranged with a ring-shaped protrusion 340 arranged coaxial with the central passage 336. A pushing element 342 is arranged in the tubular body 328. It comprises a cylindrical body 344 having a diameter somewhat smaller than the central passage 336 of the transversal wall 330 and is arranged to fit therein. Three arms 346 are arranged on the cylindrical body 344, designed and arranged to fit into the slits 338 of the transversal wall 330. The outer ends of the arms 346 are arranged with proximally and distally extending protrusions 348.

Further, a communication unit 349 is provided in the activator unit 326. The communication unit 349 comprises an electronics module in turn comprising a first circuit board 350 having a generally round shape to fit inside the tubular body 328 of the activator unit 326. The first circuit board 350 is arranged with an electric circuit 352, FIG. 22, to which a switch 354 is connected, which switch 354 is operable by the pushing element 342 as will be described. The first circuit board 350 is further arranged with an antenna chip 356 electrically connected to the electronic circuit 352 and arranged to transmit and receive data as will be described. A battery 358 is connected to the distal side of the first circuit board 350. The electronics module further comprises a second circuit board 360 arranged on the distal side of the battery 358 and provided with an electronic circuit 362. A bridge 364 with electrical wiring is arranged for interconnecting the electronic circuits of the circuit boards. A microcontroller 365 may be arranged, which also may incorporate data storage elements. A communication circuit 366 such as a Bluetooth circuit may further be arranged on the second circuit board 360. Also, a user interface 368 may further be provided, for providing visual, audible or tactile information.

An activation force element that in the embodiment shown is a spiral spring 370 having the function as a dome spring, hereafter named activation spring, is arranged to the distally directed surface of the second circuit board 360 and a proximally directed surface of an end wall 372 of an end cap 374 of the activator unit 326, which end cap 374 is attachable to the body 328 with suitable attachment elements. The activation spring 370 urges the unit with the two circuit boards 350, 360 and the battery 358 in the proximal direction together with the pushing element 342 so that its cylindrical body 344 is moved in the proximal direction in the central passage 336 and the arms 346 enter the slits 338.

The device is intended to function as follows. When the power unit 64 is to be assembled, the guide rod 322 and the drive spring 316 are pushed into the actuator 290 from the proximal end until the support plate 320 of the guide rod 322 comes in contact with the proximally directed surface of the end wall 312 of the actuator. The plunger rod 314 is then pushed into the actuator 290, tensioning the drive spring 316, until the inwardly directed ledges 300 of the tongues 294 of the actuator enter the annular groove 324 of the plunger rod 314.

The holding element 266 is pushed onto the plunger rod 314 from the proximal direction until the ledges 274 of the holding element 266 also engage with the annular groove 324 of the plunger rod 314 and are positioned radially inwards of the tongues 294 of the actuator 290. Then the actuator sleeve 276 is pushed in the proximal direction onto the actuator 290, thereby preventing the ledges 300 of the tongues 294 of the actuator 290 as well as the ledges 274 of the holding element 266 from escaping the annular groove 324 of the plunger rod 314.

Figure 23:
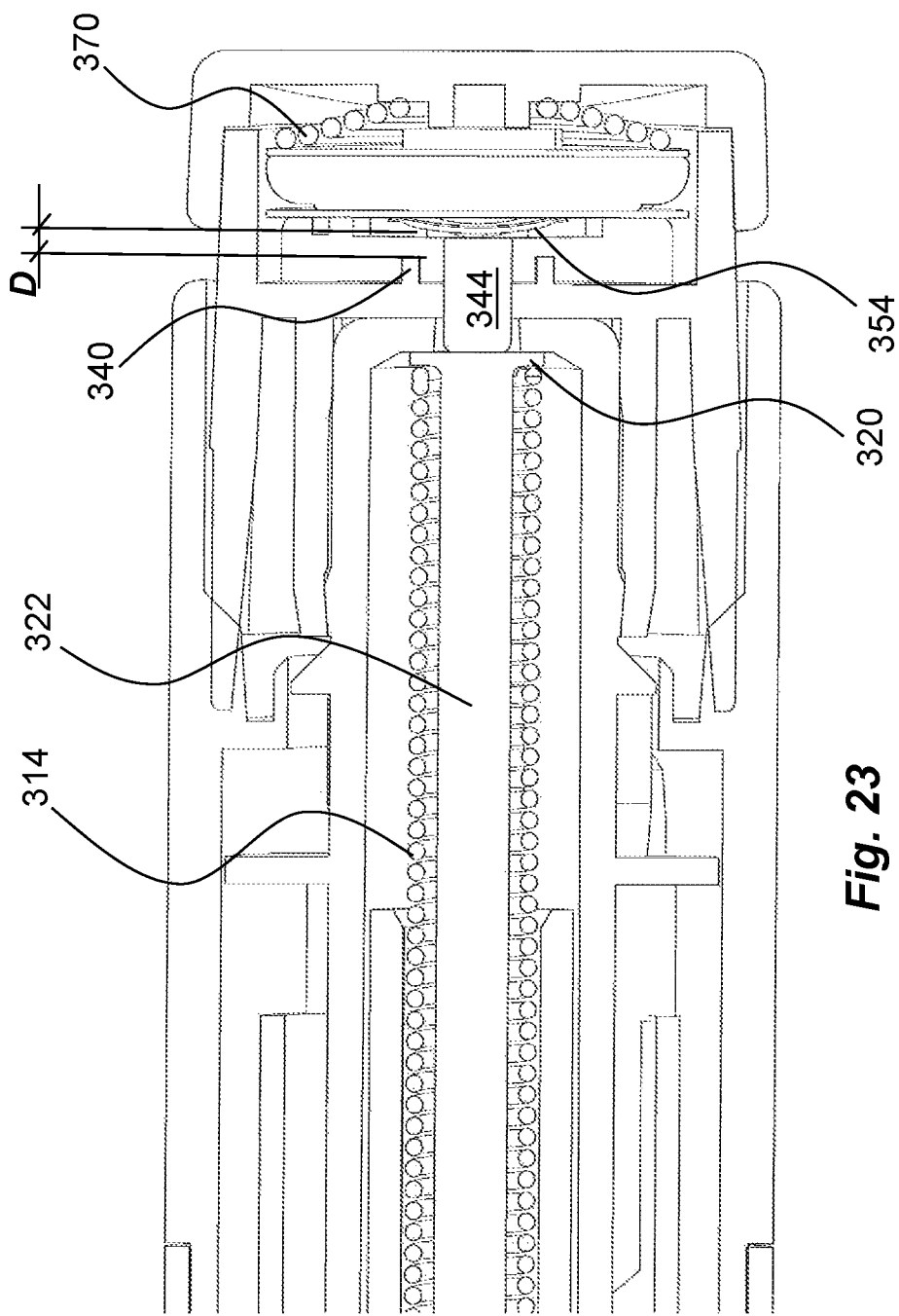

The activator unit 326 is then attached to the distal end 310 of the actuator 290 with suitable attachment elements (not shown). When attaching the activator unit 326, the cylindrical body 344 of the pushing element 342 enters the central passage 313 of the end wall 312 of the actuator and comes in contact with the distal surface of the support plate 320. Since the force of the tensioned drive spring 316 is much higher than the force of the activation spring 370, the pushing element 342 as well as the communication unit 349 will be moved distally in relation to the housing to the non-activated position, tensioning the activation spring 370 and creating a distance D between the switch 354 and the annular contact the ring-shaped protrusion 340 of the transversal wall 330 as seen in FIG. 23. The arms 346 of the pushing element 342 with their distally directed protrusions 348 will create a force distribution on the communication unit 349. In the initial non-activated position, the activator unit cannot be pressed or moved in the proximal direction in relation to the rest of the medicament delivery device because the ledges 308 of the arms 306 engage with the annular ledge 225 of the central wall 222 as seen in FIG. 17a.

When the medicament delivery device is to be used, a medicament container 226 is placed in the container holder 252 and the assembly is placed in the proximal housing part 216. The distal housing part 218 with the power unit 264 is then interconnected and locked to the proximal housing part by the attachment elements 219, 220. Further, the inwardly directed ledges 262 at the distal end of the medicament container holder 252 engage with the annular ledge 270 of the holding element 266, interconnecting them. The device is now ready to use. Also the distal part of the medicament delivery member guard 234 will surround the actuator sleeve 276 wherein the inclined tongues 248 will pass the ledge 280 providing a lock in the longitudinal direction of between the medicament delivery member guard 234 and the actuator sleeve 276.

When a dose of medicament is to be delivered to a user, the proximal end of the medicament delivery device and thus the medicament delivery member guard 234 is pressed against a dose delivery site. Now the medicament delivery device, apart from the stationary medicament delivery member guard and the inter-connected actuator sleeve 276, is moved in the proximal direction until the distal end of the actuator sleeve 276 comes in contact with the central wall 222 of the distal housing part 218, FIG. 24, wherein the movement is stopped. At the same time, the distal end of the actuator sleeve 276 has come in contact with the wedge-shaped protrusions 309 on the outer surface of the arms 306, whereby the arms 306 flex radially inwards, which will bring the ledges 308 at the free ends of the arms radially inside the ledge 225 of the central wall 222 of the distal housing part 218.

Figure 24:
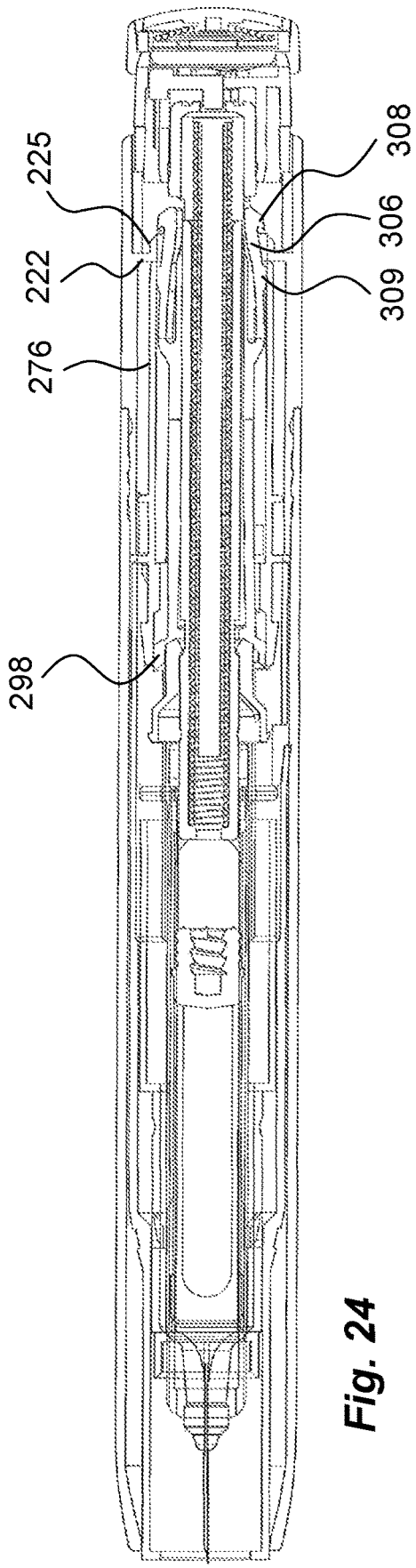
Figure 25:
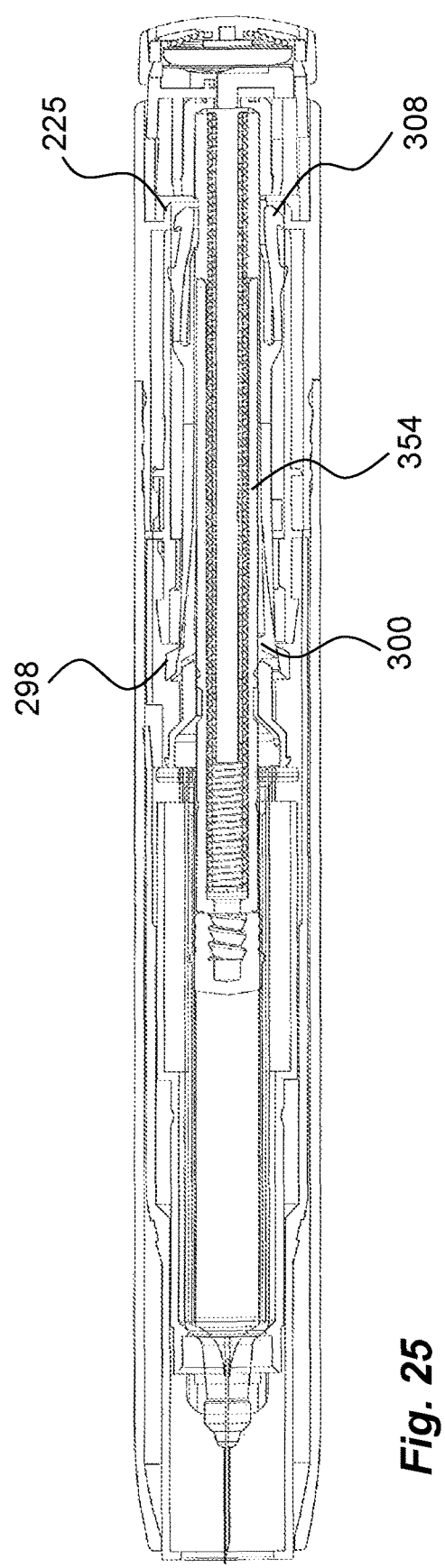

The movement of the actuator 290 in relation to the actuator sleeve 276 has caused the band-shaped part 298 to protrude to some extent out of the proximal end of the actuator sleeve 276, FIG. 24, setting the power unit in a first activation state. When the user now presses on the activator unit 326 in the proximal direction the actuator 290 is moved in the proximal direction because of the direct connection between them, whereby the ledges 308 of the arms 306 of the actuator 290 pass the annular ledge 225 of the central wall 222, FIG. 25. Because of the engagement of the actuator 290 with its ledges 300 in the annular groove 324 of the plunger rod 314, also the plunger rod 314 will move in the proximal direction as well as the holding element 266. The movement of the actuator 290 will cause the band-shaped part 298 to be moved completely out of the actuator sleeve 276, FIG. 25, and because of the resilient properties of the tongues 294 of the actuator 290, the ledges 300 will move out of the annular groove 324 of the plunger rod 314, thereby releasing the plunger rod 314.

Due to the force of the drive spring 316, the plunger rod 314 is urged in the proximal direction. Since the ledges 274 of the holding element 266 is still in the annular groove 324 and the holding element 266 is connected to the medicament container holder 252, the medicament container holder 252 and the medicament container 226 with its medicament delivery member 230 will be moved in the proximal direction, when the plunger rod 314 is moved in the proximal direction, causing a penetration of the medicament delivery member 230 into the tissue of the patient. The movement of the medicament container holder 252 and the medicament container 226 is stopped when the proximally directed surfaces surrounding the neck portion 254 abut a ledge on the inner surface of the proximal housing part 216. It may also be that the force of the drive spring 316 will urge the plunger rod 314 in the proximal direction with such a force that the ledges of the holding element are forced out of the annular groove 324. However, since the plunger rod 314 is acting on the stopper 228 and due to the incompressibility of the medicament inside the medicament container 226 as well as the small passage in the medicament delivery member 230, the medicament container 226 with its container holder 252 will be moved in the proximal direction causing a penetration of the medicament delivery member 230 into the tissue of the patient.

The plunger rod 314 is urged further in the proximal direction wherein the ledges 274 of the holding element 266 will be forced out of engagement with the annular groove 324 due to the flexing properties of the tongues 272 of the holding member. The plunger rod 314 will now act on the stopper 228 inside the medicament container 226, whereby a dose of medicament will be expelled through the medicament delivery member 230, FIG. 27. The communication unit 349 may now be activated. In order to do this, the force of the activation spring 370 is chosen such that it overcomes the force of the drive spring 316 at a certain extension point of the drive spring 316 and thus a certain position of the plunger rod 314. This position may for instance be when the plunger rod 314 and the stopper 228 have come close to their most proximal position close to the proximal end of the medicament container 226.

Figure 26:
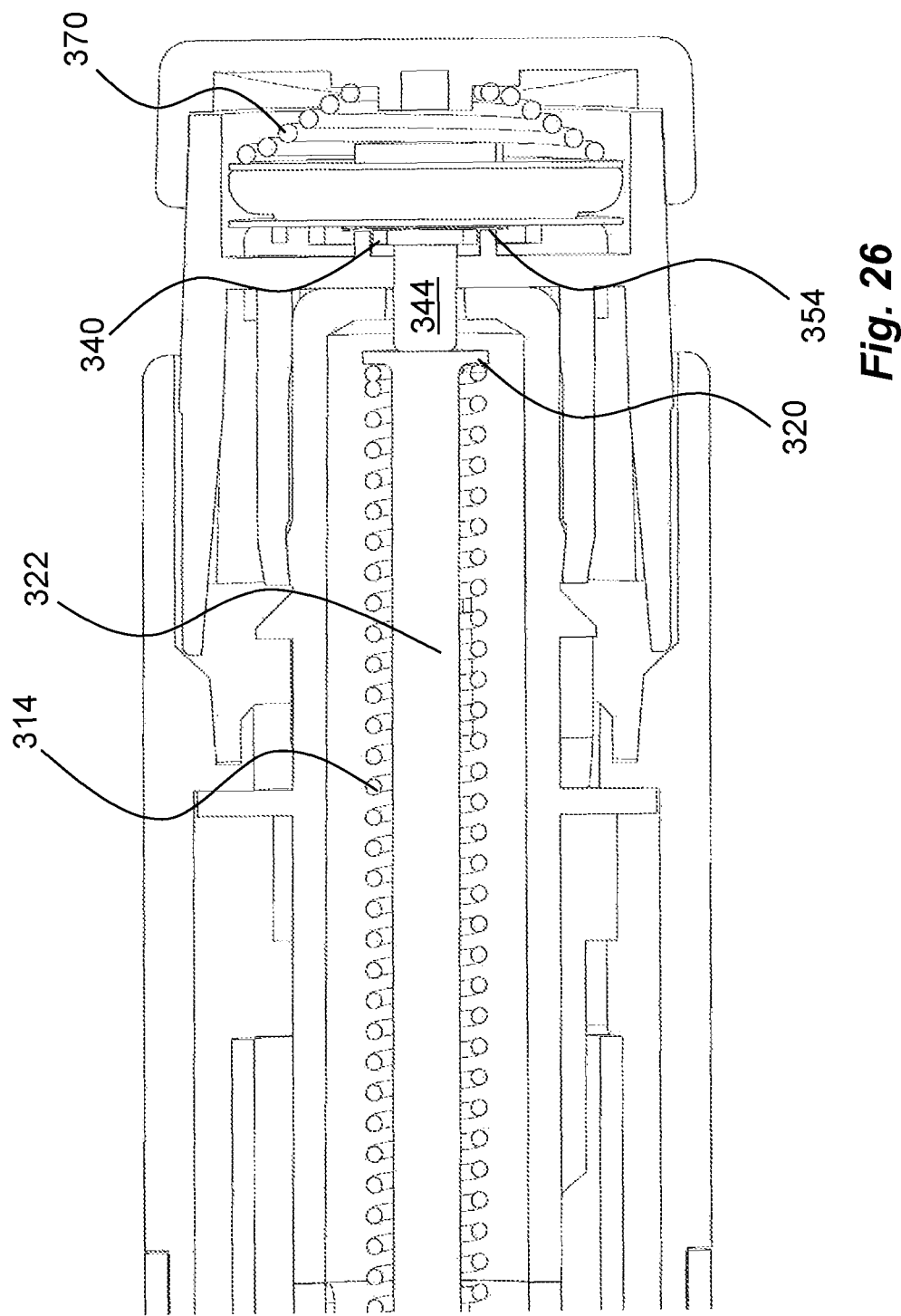

When now the force of the activation spring 370 of the monitoring unit is higher than the force of the drive spring 316, the spring 370 will move the communication unit 349 in the proximal direction the distance D until the switch 354 is moved in contact with the ring-shaped protrusion 340 to the activated position, FIG. 26, whereby the switch 354 activates the electric circuits of the circuit boards 350, 360 to perform functions as will be described below. In this context, it is to be understood that the activation force element 370 may be of many other designs capable of providing the necessary force to move the communication unit to the active position, including other types of springs, elements having resilient properties like rubber, plastic with resilient properties etc.

The user may now remove the medicament delivery device from the dose delivery site. This will cause actuator sleeve 276 and the medicament delivery member guard 234 to be moved in the proximal direction due to the force from the medicament delivery member guard spring 315 acting on the actuator sleeve 276 and because of the connection between the actuator sleeve 276 and the medicament delivery member guard 234, which movement will cause the medicament delivery member 230 to be shielded. In the extended position, the medicament delivery member guard 234 is locked because when the actuator sleeve 276 is moved in the proximal direction by the medicament delivery member guard spring 315, the band-shaped part 298 of the tongues 294 of the actuator 290 will pass the distally directed surfaces 289 of the ribs 287 and flex in the radial direction as seen by the arrows, FIG. 28, hitting the inner surface of the actuator sleeve 276. Thus, any attempt to push the medicament delivery member guard 234 in the distal direction will be stopped by the tongues 294 of the actuator 290 in contact with the distal surfaces 289 of the ribs 287. Further, the hitting of the band-shaped part 298 on the inner surface of the actuator sleeve 276 will cause an audible as well as tactile signal that the medicament delivery member guard 234 is locked.

According to the disclosure, the activation of the communication unit may cause a number of functions to be performed, all depending on the intended and desired use of the device. According to one aspect of the disclosure the switch 354, when activated, will for example trigger the microcontroller 145, 365 of the electronics module by connecting it to a suitable power source 150, 358 arranged in the device, such as a battery like a button cell or the like. Other types of power sources may be piezo elements, solar cell panels or the like. The microcontroller 145, 365 is arranged to control at least one of the communication circuits 60, 160, 366.

The electronics module of the communication units may now perform a number of different functions either alone or in combination with other functions. One basic function that the electronics module may perform is to register the end of dose signal generated when the switches are activated as described above.

In one basic function, the end of dose signal may be communicated directly to the user of the device such that it is safe to remove the medicament delivery device. This communication may be done visually, e.g. by text stored in the electronics module that is displayed on a suitable display 154, 376 on the device. In addition to, or instead, the communication may be performed audibly, e.g. by a recorded message stored in the electronics module that is played in an appropriate loudspeaker 156, 368 of the electronics module or of the medicament delivery device as such.

The electronics module may be provided with a delay function that will delay the output to a user after the switch has been activated. The reason for the delay function may be to ascertain that a dose of medicament has been completely delivered before the user withdraws the medicament delivery device. Regarding the embodiment with the monitoring unit spring, the delay function may provide a possibility of not being forced to use tight tolerances regarding spring forces and at which position of the plunger rod the force is switched and the communication unit is activated. If the delay is set to handle a range of positions where the monitoring unit may be activated, it is ensured that the complete dose has been delivered when the user receives the end of dose message.

The electronics module may further be arranged with some sort of clock or timing function in order to obtain a time stamp when an end of dose signal has been generated. This information may be stored in the data storage elements of the micro controller. With a time stamp, it is possible to obtain information when a specific dose has been administered and also to calculate when a subsequent dose is to be delivered based e.g. on pre-stored data regarding a prescription scheme. This information may then be directly communicated to the user. Further, additional sensors may be provided such as miniaturized piezo-electric sensors that may be used to sense and monitor force levels between different components of the medicament delivery device.

The electronics unit may further be arranged to handle and provide additional information to a user based on the end of dose activation. For example, if the device is a disposable injection device, the user may after completed dose delivery be prompted to discard the device in a safe way, e.g. placing it in a safe container. In addition, the information may ask the user to attach a protective cap on the medicament delivery member in order to avoid damages. On the other hand, if the device is a reusable, the information may be to replace the used medicament container with a new container in order to make the device ready for a subsequent dose delivery. Also, the user may be prompted to remove the used medicament delivery member and to replace it with a new, sterile medicament delivery member.

Regarding communication of data, the electronics module may be arranged with a communication circuit that is capable of communicating with other devices, preferably wireless. Feasible communication systems are near range wireless communication technologies such as Bluetooth, ANT and the like as well as RFID and NFC technologies. When this type of communication technologies are used, the monitoring unit is preferably connected to a smart device capable of communicating with the communicating circuit of the monitoring unit and to obtain information from the monitoring unit. When a smart device is used, then the built-in user interface of the smart device may preferably be used, such as its display, loudspeakers and microphone. Also, the smart phone may be provided with programs capable of handling data from the monitoring unit and to calculate and communicate subsequent dose delivery operations to a user.

Further, the built in communication systems of the smart device may be used for transmitting data obtained from the monitoring unit and possibly processed by the smart device to external databases and information collection and processing sources. The communication systems are preferably mobile communication systems such as GSM, 4G, 5G, wlan etc. In this respect, instead of having a program or an application stored in the smart device, the smart device may connect to suitable sites on the internet, where the appropriate information may be presented to the user.

A suitable receiver may be databases set up for handling information from medicament delivery devices. The databases may be set up to communicate back to the user via the communication unit of the medicament delivery device, providing the user with specific information. In this respect, the information may be transmitted from the databases via the wireless networks, or may be stored beforehand in the communication unit and activated by a transmitted signal from the databases. This scheme may be stored in the electronics module, or in the smart device or in the cloud and down-loaded to the medicament delivery device or the smart device upon activation.

The information from the electronics module may include features that are important to for example a physician of the patient/user. The information may then include event data such as time and date when the medicament was delivered to the user. In this respect, the activation of the electronics module may trigger the recording/logging of the date and time of the activation. This storage may be done in the electronics module if it has the means of obtaining such information from outside the medicament delivery device. Further, the information may be stored on the internet in that a signal from the electronics module, either direct or via a smart device, will trigger a time and date registration on a computer or in a database connected to the internet.

Even though the medicament delivery devices have been described in connection with a medicament container filled with a treatment drug, it is to be understood that the medicament container could be a so called dummy that does not contain any medicament and that can be used for tutorial purposes. It is further to be understood that the communication unit may be integrated in the medicament delivery device, but it may also be arranged as a separate unit that could be connectable to the medicament delivery device; an add-on.

It is to be understood that the embodiments described above and shown in the drawings are to be regarded only as non-limiting examples of the disclosure and that it may be modified in many ways within the scope of the patent claims.

The invention claimed is:

1. A medicament delivery device comprising:
   a housing, which housing is arranged to accommodate a medicament container;
   a drive mechanism comprising a drive force element, which drive mechanism is capable of, upon activation, act on the medicament container for delivering a dose of medicament from the medicament container;
   a communication unit associated with the housing; and
   a pushing element comprising radially extending arms that are operably connected between a distal end of the drive force element and a proximally directed surface of the communication unit and that comprise distally extending protrusions for providing force distribution on the communication unit;
   a switch operably connectable to the drive mechanism and connected to the communication unit for activating the communication unit when operated,
   wherein the switch is operated by the drive mechanism during a dose delivery sequence.

2. The medicament delivery device according to claim 1, wherein the communication unit is movable in the longitudinal direction between a non-activated position and an activated position, wherein the drive force element is arranged to bias the communication unit in the distal direction towards the non-activated position, an activation force element arranged to exert a force on the communication unit in the proximal direction, wherein the force exerted by the activation force element is chosen such that its force exceeds the bias from the drive force element during a dose delivery sequence, thereby moving the communication unit to the activated position.

3. The medicament delivery device according to claim 2, wherein the force exerted by the activation force element is chosen such that its force exceeds the force from the drive force element near the end of a dose delivery sequence, thereby moving the communication unit to an activated position.

4. The medicament delivery device according to claim 2, wherein the switch is positioned on a proximally directed surface of the communication unit, that the medicament delivery device is arranged with a distally directed contact surface, wherein the switch is moved in contact with the distally directed contact surface when the communication unit is moved to the activated position.

5. The medicament delivery device according to claim 1, wherein the drive force element is a compression spring.

6. The medicament delivery device according to claim 5, further comprising a spring guide rod, which spring guide rod is arranged with a support element at its distal end, wherein the compression spring rests against a proximally directed surface of the support element and wherein the pushing element is in contact with a distally directed surface of the support element.

7. The medicament delivery device according to claim 1, wherein activation of the communication unit will cause the communication unit to retrieve information and to transmit the information to a receiver.

8. The medicament delivery device according to claim 7, wherein the communication unit is arranged with a delay function providing a delay between activation of the communication unit and transmission of retrieved information.

9. The medicament delivery device according to claim 7, wherein the communication unit is arranged with a timing function providing a time stamp of the activation of the communication unit.

10. The medicament delivery device according to claim 1, wherein the communication unit is arranged to communicate directly with a user being a receiver of information from the communication unit.

11. The medicament delivery device according to claim 10, wherein the communication is audible, tactile and/or visual.

12. The medicament delivery device according to claim 1, wherein the communication unit is arranged to communicate via a smart device to receivers, which receivers are users and/or external, cloud-based, data retrievers.

13. The medicament delivery device according to claim 1, wherein the communication unit is arranged to communicate with wireless networks and/or mobile communication networks, comprising transmitting and receiving data.

14. The medicament delivery device according to claim 1, wherein the communication unit is integrated in the medicament delivery device or arranged as a separate unit connectable to the medicament delivery device.

15. A medicament delivery device comprising:
    a housing, which housing is arranged to accommodate a medicament container;
    a drive mechanism comprising a drive force element, which drive mechanism is capable of, upon activation, act on the medicament container for delivering a dose of medicament from the medicament container;
    a communication unit associated with the housing;
    an activation force element; and
    a switch operably connectable to the drive mechanism and connected to the communication unit for activating the communication unit when operated,
    wherein the switch is operated by the drive mechanism during a dose delivery sequence
    wherein the drive force element biases the communication unit in a distal direction towards a non-activated position and the activation force element exerts a force on the communication unit in a proximal direction,
    wherein the force exerted by the activation force element exceeds the bias from the drive force element during a dose delivery sequence to move the communication unit to the activated position.

16. The medicament delivery device of claim 15, wherein the switch is positioned on a proximally directed surface of the communication unit and where a distally directed contact surface contacts the switch when the communication unit is moved to the activated position.

17. The medicament delivery device of claim 16, wherein the drive force element is a compression spring, wherein the medicament delivery device further comprises a pushing element operably connected between a distal end of the compression spring and the proximally directed surface of the communication unit.

18. The medicament delivery device according to claim 17, wherein the pushing element is arranged with a number of generally radially extending arms having extending protrusions for providing force distribution on the communication unit.

19. The medicament delivery device according to claim 15, wherein the communication unit is integrated in the medicament delivery device or arranged as a separate unit connectable to the medicament delivery device.

* * * * *